United States Patent
Matityahu et al.

(10) Patent No.: US 8,951,295 B2
(45) Date of Patent: Feb. 10, 2015

(54) POSTERIOR SPINAL FASTENER

(75) Inventors: Amir M. Matityahu, Los Altos, CA (US); Robert Trigg McClellan, San Francisco, CA (US); William H. Dillin, Rancho Palos Verdes, CA (US)

(73) Assignee: Total Connect Spine, LLC, Rancho Palos Verdes, CA (US)

( * ) Notice: Subject to any disclaimer, the term of this patent is extended or adjusted under 35 U.S.C. 154(b) by 1116 days.

(21) Appl. No.: 12/426,898

(22) Filed: Apr. 20, 2009

(65) Prior Publication Data

US 2010/0016903 A1 Jan. 21, 2010

Related U.S. Application Data

(60) Provisional application No. 61/046,762, filed on Apr. 21, 2008.

(51) Int. Cl.
*A61B 17/84* (2006.01)
*A61B 17/86* (2006.01)
(Continued)

(52) U.S. Cl.
CPC .......... *A61B 17/8625* (2013.01); *A61B 17/70* (2013.01); *A61B 17/866* (2013.01); *A61B 17/8685* (2013.01); *A61B 17/1642* (2013.01); *A61B 17/1671* (2013.01); *A61B 17/7001* (2013.01); *A61B 17/7035* (2013.01); *A61B 17/7049* (2013.01); *A61B 17/7098* (2013.01); *A61B 17/864* (2013.01)
USPC ....................................... 606/329

(58) Field of Classification Search
CPC .................................................. A61B 17/7035
USPC .................. 606/329; 623/17.11, FOR. 17
See application file for complete search history.

(56) References Cited

U.S. PATENT DOCUMENTS

| | | | |
|---|---|---|---|
| 4,653,489 A | 3/1987 | Tronzo | |
| 4,790,303 A | 12/1988 | Steffee | |

(Continued)

FOREIGN PATENT DOCUMENTS

| | | |
|---|---|---|
| FR | 2743290 A1 | 1/1996 |
| WO | 0160270 | 8/2001 |

(Continued)

OTHER PUBLICATIONS

Dec. 4, 2009 International Search Report issued by the U.S. Patent and Trademark Office in the roll of ISA/US for corresponding PCT application serial No. PCT/US2009/059905, p. 1.

(Continued)

*Primary Examiner* — David H Willse
(74) *Attorney, Agent, or Firm* — Intellectual Innovations Legal Advisors

(57) ABSTRACT

A posterior spinal fastener is disclosed for insertion into a vertebra of a mammalian body, the vertebra having posterior elements and a vertebral body. The fastener includes an elongate member adapted for insertion into the vertebra. The elongate body has an anterior portion and a posterior portion. The anterior portion is arcuate in shape for placement in the vertebral body. The posterior portion has a length so as to be accessible at the posterior elements of the vertebra when the anterior portion is disposed in the vertebral body. A method of use of the posterior spinal fastener is also disclosed, in which the posterior spinal fastener is introduced into the vertebra at the posterior elements and arcuately extended into the vertebral body.

19 Claims, 25 Drawing Sheets

(51) Int. Cl.
*A61B 17/70* (2006.01)
*A61B 17/16* (2006.01)

(56) References Cited

U.S. PATENT DOCUMENTS

| | | | |
|---|---|---|---|
| 5,176,679 | A | 1/1993 | Lin |
| 5,690,630 | A | 11/1997 | Errico et al. |
| 5,989,250 | A | 11/1999 | Wagner et al. |
| 6,063,089 | A | 5/2000 | Errico et al. |
| 6,325,805 | B1 | 12/2001 | Ogilvie et al. |
| 6,533,790 | B1 | 3/2003 | Liu |
| 6,749,614 | B2 | 6/2004 | Teitelbaum et al. |
| 6,755,830 | B2 | 6/2004 | Minfelde et al. |
| 6,887,241 | B1 | 5/2005 | McBride et al. |
| 6,923,811 | B1 | 8/2005 | Carl et al. |
| 7,585,314 | B2 | 9/2009 | Taylor et al. |
| 2002/0068975 | A1 | 6/2002 | Teitelbaum et al. |
| 2003/0028192 | A1 | 2/2003 | Schar et al. |
| 2003/0045879 | A1 | 3/2003 | Minfelde et al. |
| 2003/0171755 | A1 | 9/2003 | Moseley et al. |
| 2004/0186473 | A1 | 9/2004 | Cournoyer et al. |
| 2005/0055027 | A1 | 3/2005 | Yeung et al. |
| 2005/0080415 | A1 | 4/2005 | Keyer et al. |
| 2005/0113831 | A1 | 5/2005 | Franck et al. |
| 2005/0197660 | A1 | 9/2005 | Haid, Jr. et al. |
| 2005/0228382 | A1 | 10/2005 | Richelsoph et al. |
| 2005/0240266 | A1 | 10/2005 | Kuiper et al. |
| 2005/0246023 | A1* | 11/2005 | Yeung .................. 623/17.11 |
| 2005/0261770 | A1 | 11/2005 | Kuiper et al. |
| 2005/0267481 | A1 | 12/2005 | Carl et al. |
| 2006/0084982 | A1 | 4/2006 | Kim |
| 2006/0195094 | A1 | 8/2006 | McGraw et al. |
| 2006/0200151 | A1 | 9/2006 | Ducharme et al. |
| 2006/0235389 | A1 | 10/2006 | Albert et al. |
| 2006/0235414 | A1 | 10/2006 | Lim et al. |
| 2006/0247600 | A1* | 11/2006 | Yeung et al. .................. 604/500 |
| 2006/0247626 | A1 | 11/2006 | Taylor et al. |
| 2006/0271054 | A1 | 11/2006 | Sucec et al. |
| 2008/0177317 | A1 | 7/2008 | Jackson |
| 2010/0016903 | A1 | 1/2010 | Matityahu et al. |
| 2010/0094346 | A1 | 4/2010 | Matityahu |

FOREIGN PATENT DOCUMENTS

| | | |
|---|---|---|
| WO | 2007/041648 | 4/2007 |
| WO | WO 2007/053960 A1 | 5/2007 |
| WO | 2008/021319 | 2/2008 |
| WO | WO-2008128067 A2 | 10/2008 |

OTHER PUBLICATIONS

Dec. 4, 2009 Written Opinion of the International Searching Authority issued by the U.S. Patent and Trademark Office in the roll of ISA/US for corresponding PCT application serial No. PCT/US2009/059905, pp. 1-6.

Jun. 17, 2009 International Search Report issued by the U.S. Patent and Trademark Office in the roll of ISA/US for corresponding PCT application serial No. PCT/US2009/041160, p. 1.

Oct. 26, 2010 International Preliminary Report on Patentability issued by the U.S. Patent and Trademark Office in the roll of ISA/US for corresponding PCT application serial No. PCT/US2009/041160, pp. 1-7.

Nov. 25, 2011 Restriction Requirement issued by the U.S. Patent Office, Issued for U.S. Appl. No. 12/575,396 on Nov. 25, 2011 by the USPTO, pp. 1-7.

Feb. 6, 2012 Official Action issued by the U.S. Patent Office, Issued for U.S. Appl. No. 12/575,396 on Feb. 6, 2012 by the USPTO, pp. 1-17.

Official Action Chinese Patent Office with English Translation, Chinese Patent Application No. 200980120156.0, McKesson Reference, pp. 1-8, Feb. 28, 2012.

Instructions for response to Action for corresponding Chinese Patent Application No. 200980120156.0, McKesson Reference, pp. 1-11, Aug. 27, 2012.

Response to Feb. 6, 2012 Non-Final Office Action, correspond U.S. Appl. No. 12/575,396, McKesson Reference, pp. 1-14.

Response to Nov. 25, 2011 Restriction Requirement corresponding U.S. Appl. No. 12/575,396 McKesson Reference, p. 1.

Supplementary European Search Report issued by the European Patent Office for EP patent application Serial No. EP09819848, (Jul. 9, 2013) pp. 1-8.

Supplementary European Search Report issued by European Patent Office for EP patent application Serial No. EP09734068, (Jul. 1, 2013) pp. 1-5.

First Patent Examination Report issued by the Australian Patent Office for Australian Patent Application Serial No. 2009239515, mailed Nov. 28, 2013, pp. 1-5.

Response mailed on Aug. 2, 2013 for European office action dated Jan. 24, 2013 for Application No. EP09734068.1 filed Apr. 20, 2009, 25 pages.

* cited by examiner

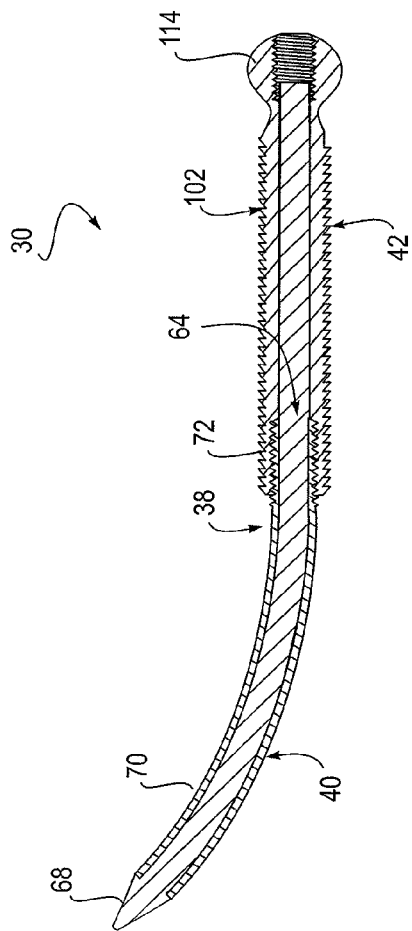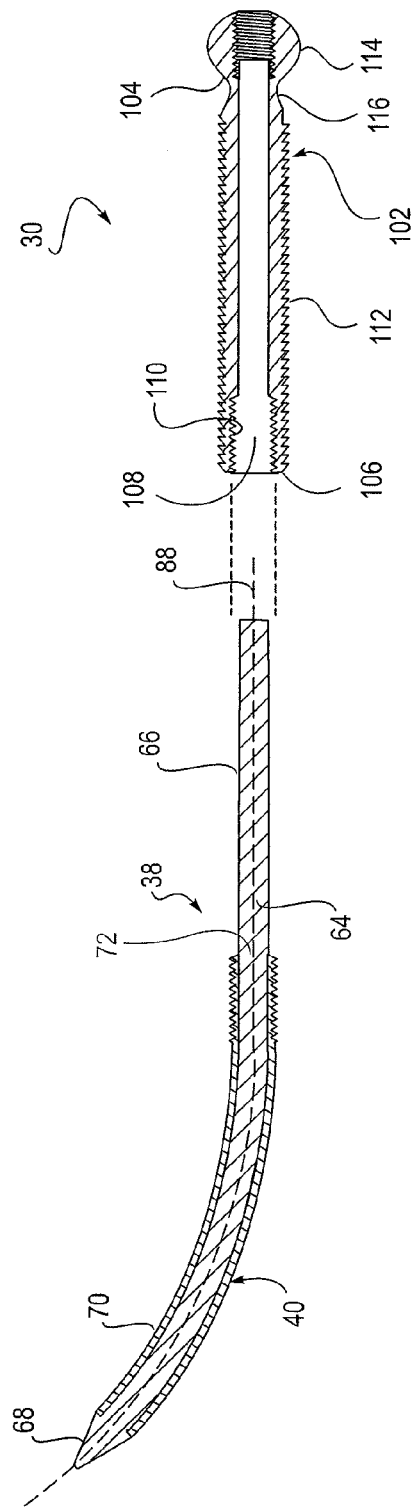

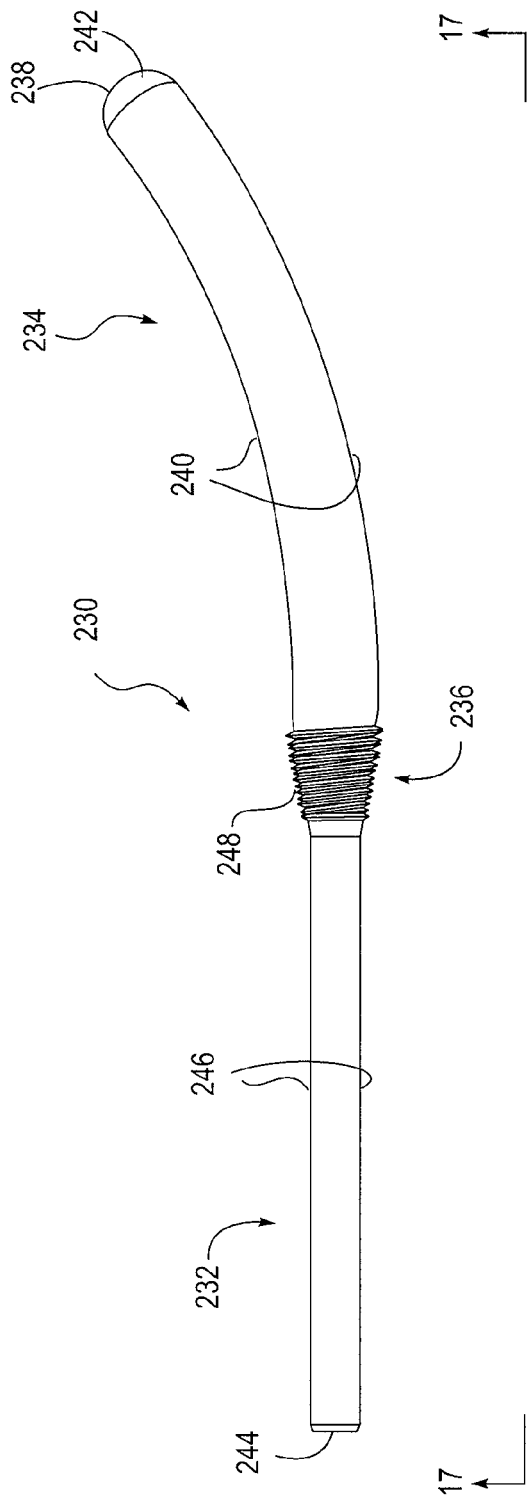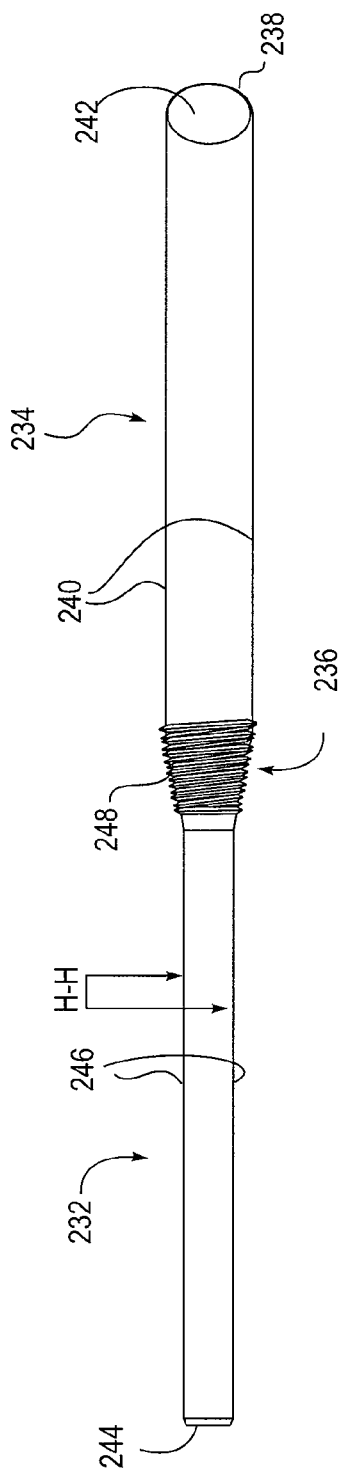

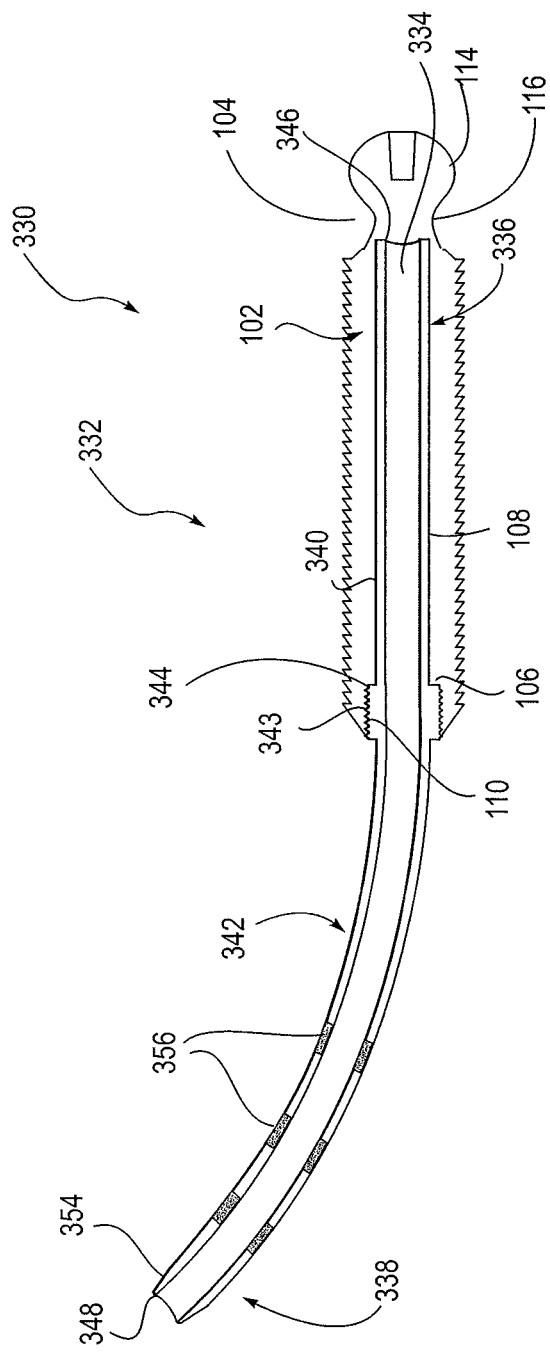
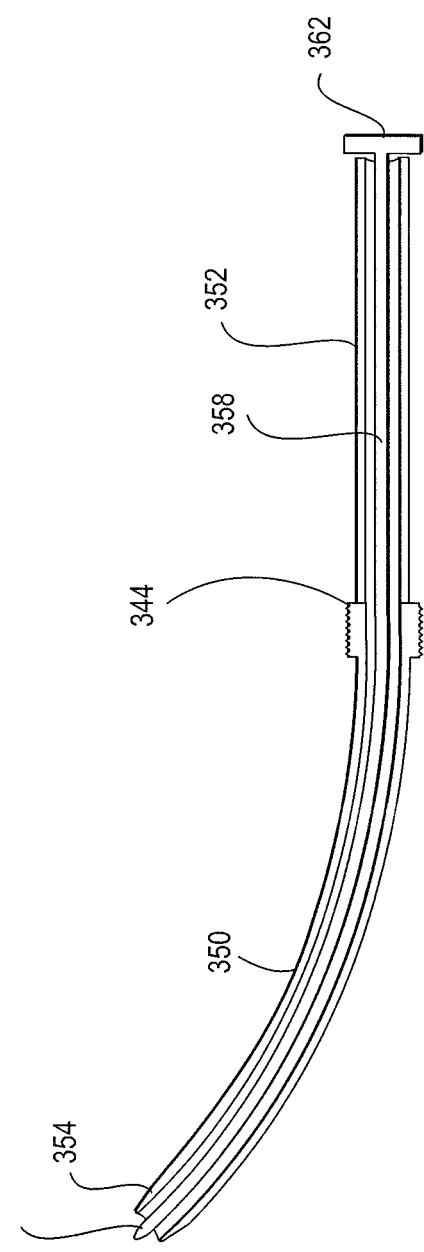
FIG. 18
FIG. 19

POSTERIOR SPINAL FASTENER

CROSS-REFERENCE TO RELATED APPLICATION

This application claims priority to U.S. Provisional Patent Application Ser. No. 61/046,762 filed Apr. 21, 2008 which is incorporated herein by this reference.

SCOPE OF THE INVENTION

The present invention relates to surgical fasteners, and in particular to posterior spinal fasteners.

BACKGROUND

As is known, spinal fusions may be indicated when there is a deformity of the spine, instability of the spine, a damaged intervertebral disk, trauma, tumor, pain, infection and/or degeneration of the spine. A number of posterior spinal fixation methods are available to instrument the spine for stabilization purposes and to allow for a fusion to occur. Commonly used devices include transpedicle and facet screws. Many transpedicle screw systems that stabilize the spine are dependent upon the pullout strength of a non-curved transpedicle screw for fixation stability. Unfortunately, transpedicular screws usually fail either by breaking at the connection between the transpedicular screw and the assembly to which it is attached, or by failure of the transpedicular screw to bone interface. A transpedicular screw can fail within the bone for multiple reasons, including osteoporotic nature of the bone, lack of fill within the pedicle, infection and/or pseudoarthrosis of the fusion mass. A straight screw is reliant upon the shear resistance that is created by the threads of the screw and the radial force created by the size of the screw relative to the inner diameter of the pedicle. In order to achieve better fixation, larger transpedicle screws are sometimes used, which may result in a fracture or perforation of the pedicle resulting in nerve root or spinal cord injury. At the upper end of instrumented construct, most transpedicle screws have to violate the normal facet joint, which may lead to an increase risk of degeneration of the adjacent disk. At the upper end of the instrumented construct, traditional transpedicle screw technique may violate the bordering facet joint creating additional mechanical driving force for adjacent segment disease and the potential for further surgery over time in that adjacent segment.

Facet screws are also commonly known and rely on the pullout strength of the screw to achieve stability. Like transpedicular screws, facet screws are typically straight and rely upon the thread geometry and thickness of the screw to increase the amount of force needed for the screw-bone construct to fail. This is a disadvantage in osteoporotic, pathologic, or low density bone where there is less for the screws to anchor to and a decrease in the pullout strength of the screw, especially in shear. Furthermore, when inserting a transpedicle or transfacet screw, a straight screw can penetrate the side or front of the vertebral body due to the angle of insertion. The transpedicle screw may also penetrate the pedicle wall possibly injuring the exiting nerve root. This penetration may significantly risk neurological or vascular structures.

On the posterior end of the pedicle screw, a linkage that allows connection of the pedicle screw to a transverse rod and is often a tulip is provided that extends vertically along the spine. The vertical rod is attached to the tulip of each of the various screws, connecting several vertebral bodies together. The rod preferably stabilizes the vertebral canal and the spine, often to achieve a fusion of the spine for a variety of reasons, including back pain, neurological problems, fracture, curvature of the spine, degeneration of the spine and/or tumor. Thus, the screws and the tulip and rod are a mechanism often utilized for keeping the vertebral bodies in a generally fixed position relative to each other while the vertebral bodies are fused together by a bone graft. Spinal fixation systems form a scaffold with multiple fixation points in the segmental spinal anatomy. This created vertical assembly, sometimes with transverse linking, seeks to maintain spinal architecture under physiological loading while biological materials form a final union between segments within the span of this scaffold.

An additional problem with current devices is safety. The spinal cord travels behind the vertebral body. Nerves extend off the spinal cord between each of the various bodies and extend under the pedicle, or under each of the pedicles. In the thoracic spine, for instance, the spinal cord occupies a very small space within the confine of the vertebral bodies. Therefore, a very small margin of error exists anatomically when forming the scaffold function of spinal instrumentation with pedicle screws fixed to each thoracic vertebral level. In the lumbar spine, the nerves float in a spinal fluid sac exiting at each spinal level to perform critical motor and /or sensory functions in the lower extremities and for normal control and function of the bowel and bladder. Since the screw must fit closely to the diameter of the pedicle to occupy its volume and thus have biomechanical strength, the margin of error is minimal. In other words, the technique of delivery of pedicle screws in the thoracic and lumbar spine carries inherent risk to the geometry of design of the pedicle and screw and the vector of placement into the vertebra. When a physician performs spinal surgery in the lumbar spine, a pedicle screw can perforate or extend through the side of the pedicle and touch the nerve so as to cause nerve damage. This particular problem often occurs in the medial and/or inferior quadrant of the pedicle, where the nerve route most closely contacts the pedicle. When a thoracic pedicle screw is placed, medial deviation can impale the spinal cord and imprecise placement may strike the anterior vascular structures with disastrous results.

Accordingly, what is needed is a device and method for safely stabilizing adjacent vertebra in the mammalian spine.

SUMMARY OF THE INVENTION

A posterior spinal fastener and method of using same is disclosed. The posterior spinal fastener is disclosed for insertion into a vertebra of a mammalian body, the vertebra having posterior elements and a vertebral body. The fastener includes an elongate member adapted for insertion into the vertebra. The elongate body has an anterior portion and a posterior portion. The anterior portion is arcuate in shape for placement in the vertebral body. The posterior portion has a length so as to be accessible at the posterior elements of the vertebra when the anterior portion is disposed in the vertebral body. A method of use of the posterior spinal fastener is also disclosed, in which the posterior spinal fastener is introduced into the vertebra at the posterior elements and arcuately extended into the vertebral body.

BRIEF DESCRIPTION OF THE DRAWINGS

FIG. 1 is a side elevation cross-sectional view of a posterior spinal fastener according to an embodiment of the present invention.

FIG. 2 is an exploded side elevation cross-sectional view of a posterior spinal fastener of FIG. 1, showing an elongate member having the threaded oversleeve removed from the posterior portion of the elongate member.

FIG. 16 is a side elevational view of an alternative embodiment of an elongate member of the posterior spinal fastener of the present invention, showing a rigid member.

FIG. 17 is a top plan view of the elongate member of FIG. 16, taken along line 17-17 of FIG. 16.

FIG. 18 is a side elevation cross-sectional view of an alternative embodiment of an elongate member of the posterior spinal faster, showing a cannulated elongate member.

FIG. 19 is a side elevation cross-sectional view of the elongate member of FIG. 18, showing a stylet inserted within the central bore of the cannulated posterior spinal fastener.

DESCRIPTION OF THE INVENTION

Figure 3:
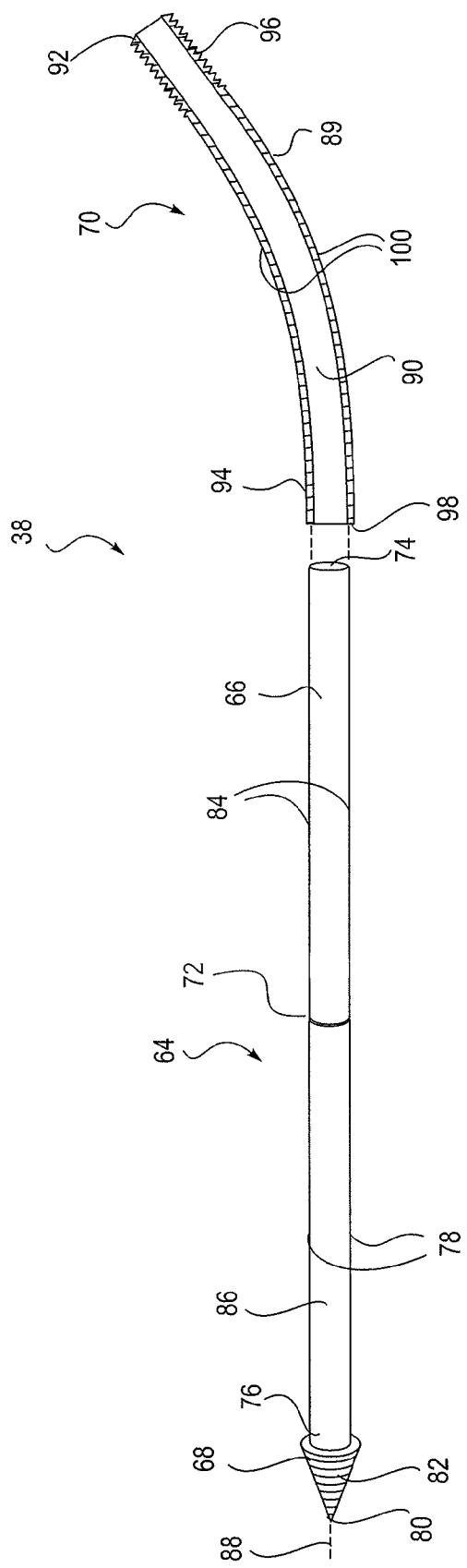
FIG. 3 is an exploded side elevation cross-sectional view of a posterior spinal fastener of FIG. 1, absent the threaded oversleeve and showing the curved oversleeve removed from the anterior portion of the elongate body.

The invention is generally directed to posterior spinal fasteners, and a system for stabilizing adjacent vertebra in a mammalian spine. As a non-limiting example, the invention may be used in association with a bone graft. Hardware is placed in the spine which will immobilize the spine while the bone solidifies or becomes one large bone mass. The system includes a curved fastener or post that can be inserted as either a transpedicular, transfacet or a laminopedicular fastening device to the posterior portion of the spine, and preferably, at or near the posterior spinal elements found in the vertebra.

More preferably, a posterior spinal fastener 30 for insertion into a vertebra 32 of a mammalian body having posterior elements 34 and a vertebral body 36 is provided (See FIGS. 1-15). The posterior spinal fastener 30 generally includes an elongate member 38 adapted for insertion into the vertebra 32. The elongate member 38 has an anterior portion 40 and a posterior portion 42, the anterior portion 40 preferably being arcuate, arciform, curved or bowed in shape for placement in the vertebral body 36 and the posterior portion 42 having a length so as to be accessible at the posterior elements 34 when the anterior portion 40 is disposed in the vertebral body 36. In a preferred embodiment, the elongate element or member 38 has a length ranging from ten to 200 millimeters, and more preferably from 20 to 60 millimeters, and a diameter of two to 20 millimeters, and more preferably 3.5 to ten millimeters. More specifically, the fastener is an apparatus for internal fixation of the spine. The apparatus includes an assembly having at least one curved spinal bone fastener 30 inserted from the lamina, through the facet joint, and/or through the pedicle, and into the vertebral body 36.

Figure 4:
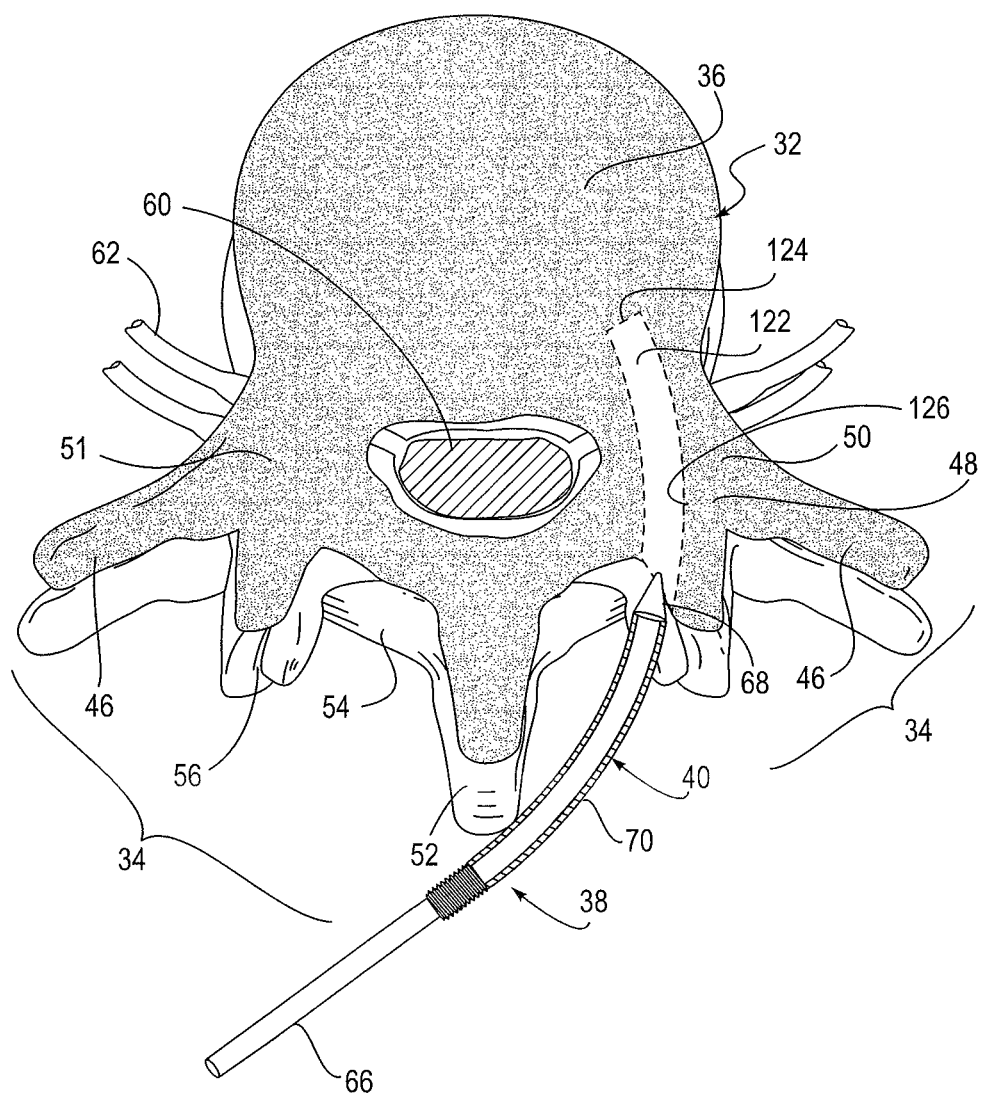
FIG. 4 is an elevational view showing positioning of an elongate member of the posterior spinal fastener of FIG. 1 in a first position for transpedicular insertion into a vertebra according to a method of use of the posterior spinal fastener.

For purposes of discussion, and as illustrated in FIG. 4, the relevant portions of the vertebra 32 will be briefly introduced. It is noted that FIG. 4, as well as FIGS. 5-13, are schematic for purposes of reference and discussion in that the portions of the elongate body, such as the anterior portion, may be visible through the curved oversleeve. The vertebra 32 includes an anterior portion or front having a vertebral body 36 and a posterior portion or back having posterior elements 34 including, for example, the vertebral arch or neural arch, transverse process(es) 46, articular process(es) 48, pedicle 50, spinous process 52, lamina 54 and facet(s) including superior and inferior facets 56, 58. The spinal cord 60 is located approximately between the anterior and posterior portions of the vertebra and includes nerve roots 62 extending therefrom.

The apparatus of an embodiment of the present invention includes an assembly having at least one curved spinal bone fastener 30 inserted through the pedicle 50 and into the vertebral body 36. The curved pedicle screw assembly, as shown in FIGS. 1-3, includes an inner non-threaded member or elongate body 64 formed by a shaft having a straight posterior portion 66 and an arcuate anterior portion 40, the shaft terminating, in at least one embodiment, at a head 68. While the system or device is specifically described to include a fastener or post that has a curvature at the anterior portion 40 or end and a straight posterior portion 42, it is also contemplated that the device may include a curvature at the posterior portion 42 or end.

The elongate member 38 may be formed by a shaft or central elongate body or elongate element 64 and a removable oversleeve 70. Generally, the shaft of elongate member 38 has a diameter that can range from one to 20 millimeters, and more preferably two to ten millimeters. The elongate element 64 is formed of a length ranging from ten to 100 millimeters and more preferably from 15 to 60 millimeters. The anterior portion 86 of the inner non-threaded member or central elongate body 64 extends from an interior portion 72, which is spaced a distance from the posterior end 74 of the central elongate body 64, to an anterior end 76 of the elongate body 64. The length of anterior portion 86 can range from five to 100 millimeters and more preferably from ten to 30 millimeters. The anterior portion may have a diameter which is the equivalent or different from the posterior portion 66. The outer surface 78 of the shaft of the anterior portion 86 may be smooth or threaded or may include a roughened surface along at least a portion thereof. The anterior portion has a substantially constant outer cylindrical surface and diameter ranging from one to 20 millimeters and more preferably from two to ten millimeters. In one embodiment, a head 68 is carried by the anterior end 76 of the elongate body 64. The head 68 may include a conical shape, which decreases in diameter toward a distal tip 80.

The head 68 has an outer maximum diameter that is greater than the substantially constant diameter of the shaft of the elongate body 64, and a pointed or anterior end 80 which has a minimum diameter that is preferably narrower than the diameter of the shaft of the elongate body 64. Preferably, the head tapers from its outer maximum diameter to its anterior end so as to form a conical arrangement. The maximum diameter of the head may range from one to 20 millimeters and more preferably from two to ten millimeters. However, variations in head dimension would not depart from the overall scope of the invention. The head 68 may also include an outer thread 82 thereon for threaded screw-type insertion, or may be composed of a substantially smooth or roughened cylindrical surface. Head 68 may also be of any other suitable shape.

As can be seen in FIG. 2, the posterior portion 66 of the fastener or post or shaft or elongate body 64 extends from an interior portion 72 of the central elongate body 64 to a posterior end 74 of the elongate body 64 or inner non-threaded member. The posterior portion 66 includes an outer or maximum substantially constant diameter which may be the equivalent of or different from the diameter of the anterior portion 86. The diameter of the shaft of the anterior portion 86 of elongate body 64 or non-threaded member can range from one to 20 millimeters, and more preferably from two to ten millimeters. The posterior portion 66 has a length so as to be accessible at the posterior elements 34 when the anterior portions 40, 86 and posterior portions 42, 66 are disposed in the vertebral body 36. The length of the posterior portion 66 can range from five to 100 millimeters and is preferably from ten to 30 millimeters. Additionally, the outer surface 84 of the posterior portion 66 may be smooth or threaded or may include a roughened surface along at least a portion thereof.

In a preferred embodiment, the inner non-threaded portion or central elongate body 64 is preferably flexible, or flexible along a portion thereof or its entire length, and more preferably, this shaft is elastic along at least its anterior portion 86 so as to bend and become arcuate in shape by the attachment of a curved oversleeve 70. The flexible or elastic elongate body 64 may have a rest position or home position having a straight configuration (see FIG. 3). Alternatively, it is contemplated that the elongate body 64 may be rigid and arcuately shaped along at least a portion thereof and, more preferably at its anterior portion 86.

The elongate body 64 may be formed of a solid material, and in one embodiment includes a cylindrical cross-section. The material used may be a shape memory material, such as a shape memory alloy, or may be a non-memory material or alloy such as titanium, stainless steel or any other material suitable for fixation of the spine. When using the memory alloy, one may design the curved member to allow for expansion of the whole or part or for a change in shape to increase the amount of force needed in anticipation of failure of the implant, bone, or both to occur. The material used may also resorb or may not resorb.

As indicated, the elongate element 38 has a central axis 88 and an anterior portion 40 and a posterior portion 42, the anterior portion 86 of elongate body 64 including an elastic body. A curved oversleeve 70 may be disposed over the anterior portion 86 for arcuately guiding the anterior portion 40 of the elongate member 38 into the vertebral body 36. The anterior portion 86 may further be rotatable about the central axis 88 within the curved oversleeve 70 for permitting screwing of the anterior portion 40 into the vertebral body 36.

Specifically, the curved pedicle fastener assembly or elongate member 38 includes a curved oversleeve 70 seated over the inner non-threaded member or elongate body 64. Preferably, the curved oversleeve 70 is placed over the flexible or arcuate portion 86 (see FIG. 2). More specifically, the inner non-threaded member 64 is received within the curved oversleeve 70. The curved oversleeve 70 may, thus, be formed by a shaft or member 89 having an outer cylindrical surface and a centralized bore 90 extending along its length which, preferably, has an inner diameter formed by the centralized bore 90 and corresponding to the outer diameter of the elongate body 64 (see FIG. 3). Preferably, the inner diameter of the curved oversleeve is a substantially constant inner diameter and ranges from one to 20 millimeters, and more preferably, from 1.5 to ten millimeters. The bore 90 is, thus, adapted to receive the inner non-threaded member or elongate body. The curved oversleeve 70 preferably has a radius of curvature ranging from two millimeters to four meters, and more preferably from ten millimeters to two meters, and most preferably ten centimeters. The radius of curvature may or may not be uniform throughout the length of the curved portion of the fastening device. As a result, the curved oversleeve 70 forms the arcuate anterior portion 40 of the elongate member 38. The outer cylindrical diameter of the curved oversleeve 70 is greater than that of the elongate body 64. Preferably, the curved oversleeve 70 has a similar outer diameter corresponding to that of the maximum diameter of the head 68 of carried by the elongate body 64. Preferably, the outer diameter of the curved oversleeve 70 ranges from one to 20 millimeters and more preferably, from two to ten millimeters and most preferably is approximately 3.5 millimeters.

The curved oversleeve 70 has a posterior end 92 and an anterior end 94 spaced therefrom. The curved oversleeve 70 has a length approximating the length of the anterior portion 86 of the elongate body 64. More preferably, the curved oversleeve 70 has a length ranging from five to 100 millimeters, and more preferably a length ranging from ten to 45 millimeters. The curved oversleeve 70 may include an outer thread surrounding at least a portion of the posterior portion 66, and preferably forms a threaded portion 96 which extends around the posterior portion 92 of the curved oversleeve 70. The anterior portion 94 or end provides a surface 98 adapted to abut the head 68 carried by the elongate body 64.

The outer cylindrical surface 100 of the curved oversleeve 70 may have a surface or portion of the surface which is composed of smooth surface or roughened surface which may allow for bone in growth. The curved oversleeve 70 is preferably rigid and may be formed of a material suitable for use in the mammalian body and spine, such as stainless steel, titanium, or other suitable material, although other materials would not depart from the overall scope of the present invention.

The curved pedicle screw assembly or elongate member 38 of a preferred embodiment may also include posterior portion 42 which is externally threaded. In the embodiment shown in FIGS. 1-3, the posterior portion 42 includes a removable second or threaded oversleeve 102. The posterior portion 66 of the elongate body 64 carries the removable threaded oversleeve 102, or more specifically, the threaded oversleeve 102 is positioned over the inner non-threaded member or elongate body 64. The threaded oversleeve 102 may also be removeably engaged with the first or curved oversleeve 70 positioned on the anterior portion 86 of the elongate body 64.

The threaded oversleeve 102 has a posterior end 104 and an anterior end 106 spaced therefrom. The threaded oversleeve 102 is a shaft having a centralized bore 108 extending along its length from its posterior end to its anterior end, which, preferably, has an inner diameter corresponding to the outer diameter of the inner non-threaded member or elongate body 64. Preferably, threaded oversleeve 102 has a length ranging from five to 105 millimeters, and more preferably from ten to 45 millimeters. The centralized bore has a substantially cylindrical cross section, the diameter or inner diameter of which ranges from one to 30 millimeters, and more preferably from 1.5 to 15 millimeters. The bore 108 is, thus, adapted to receive the elongate body 64. The threaded oversleeve 102 preferably has an inner thread 110 at its anterior end 106 that is adapted for removeably engaging the external thread 96 on the posterior portion 92 of the curved oversleeve 70. Preferably, the thread pitch on the interior or inner thread 110 of the threaded oversleeve 102 is the same as the thread pitch on the outer thread 96 of the curved oversleeve 70 so that the threaded oversleeve 102 may be advanced over the posterior portion 92 of the curved oversleeve 70. Thus, the posterior portion 92 of the curved oversleeve 70 may also be received within the bore of the threaded oversleeve 102. The threaded oversleeve 102 may also be partially or fully threaded. Specifically, the outer diameter of the threaded oversleeve 102 is formed by an outer thread 112 around a portion thereof, and preferably extends along substantially the length of the shaft of the threaded oversleeve 102. The outer diameter of the threaded oversleeve 102 is greater than that of the elongate body 64. Preferably, the outer diameter of threaded oversleeve ranges from two to 35 millimeters, and more preferably from 2.5 to 15 millimeters. Threaded oversleeve 102 may or may not be variably threaded to allow for compression of the facet joint. The threaded oversleeve 102 in one embodiment carries a tool engaging portion or head 114 at its posterior end that is shown as being ball-type or spherical in shape but may be any other suitable shape. Preferably this spherical portion 114 is spaced from the outer thread 112 by a neck 116. The spherical portion 114 is adapted to receive a tool and/or a socket or anchor or other fastening member. For example, in a preferred embodiment, the spherical portion 114 is adapted to receive a tulip 118.

While a threaded oversleeve 102 is described hereinabove, the curved pedicle screw assembly or elongate member 38 may or may not have a threaded oversleeve thereon.

A method for inserting a posterior spinal fastener 30 into a vertebra 32 of a mammalian body having a vertebral body 36 and posterior elements 34 is provided which generally includes introducing the fastener 30 into the vertebra 32 at the posterior elements 34 and arcuately extending the fastener into the vertebral body 36.

A preferred method of transpedicular insertion of the elongate member 38 of the posterior spinal fastener 30 according to the embodiment of FIGS. 1-3 is shown in FIGS. 4-8, wherein the fastener 30 is extended through the pedicle 50 for entry into the vertebral body 36. More specifically, the pedicle 50, or pedicle wall, is first prepared for insertion in the traditional fashion known in the art. For example, the entry to the pedicle 50 is located. This may include removing a piece or portion of the spinal facet from an upper pedicle so as to gain access into the pedicle 50. Subsequently, a drill (not shown) is used to drill a small hole through the exterior, most commonly, but not limited to, in the back portion of the pedicle 50, in order to penetrate the hard exterior of the pedicle 50. Then a tool, for example having a sharpened or pick-like, or flattened curved or straight end and sometimes referred to as a gear shift (not shown), is inserted by surging the tool through the drilled portion and then into the spongy bone material in the vertebral body 36 to create a bore 122 through the spongy material. The bore 122 is preferably created having a length which corresponds to at least a portion of the posterior spinal fastener 30. The bore 122 is also formed so as to curve at its anterior end 124 toward the central portion 120 of the vertebral body 36.

The gear shift generally has a diameter ranging from 2.5 to 3.5 millimeters, but, as in insertion into the sacrum or ilium, it may have a diameter of 2.5 to 15 millimeters, and may include an arcuate distal end and a straight proximal end. Preferably, only the arcuate distal end is inserted into the pedicle 50. Since the gear shift has a diameter of approximately 2.5 to 3.5 millimeters, the aperture or channel 112 created by the gear shift is less than or equal to the non-threaded member or elongate body 64 of the elongate member 38 with curved oversleeve 70 which preferably has a diameter of approximately 3.5 millimeters. More generally, a curved bore or channel 122 approximately equal or narrower in width and having a length corresponding to a portion of the curved portion of the gear shift, and thus the posterior spinal fastener, is created in the pedicle 50.

Once the channel 122 is initially formed, the inner walls of the formed channel in the pedicle 50 are palpated using a feeler or ball tipped probe (not shown) to determine whether the physician has perforated the pedicle 50.

The curved assembly or elongate member 38 is then inserted into the palpated channel 122. Preferably, the elongate member 38, including the curved rigid oversleeve 70 positioned over the flexible anterior portion 86 of the elongate body 64, is moved or inserted from a first position (shown in FIG. 4) into the bore 122 in the pedicle 50 created by the gear shift and drill. Specifically, the head 68 located at the anterior end of the spinal fastener is first inserted into the bore in the pedicle 50. The fastener is then extended through the pedicle 50 for entry into the vertebral body 36.

Figure 5:
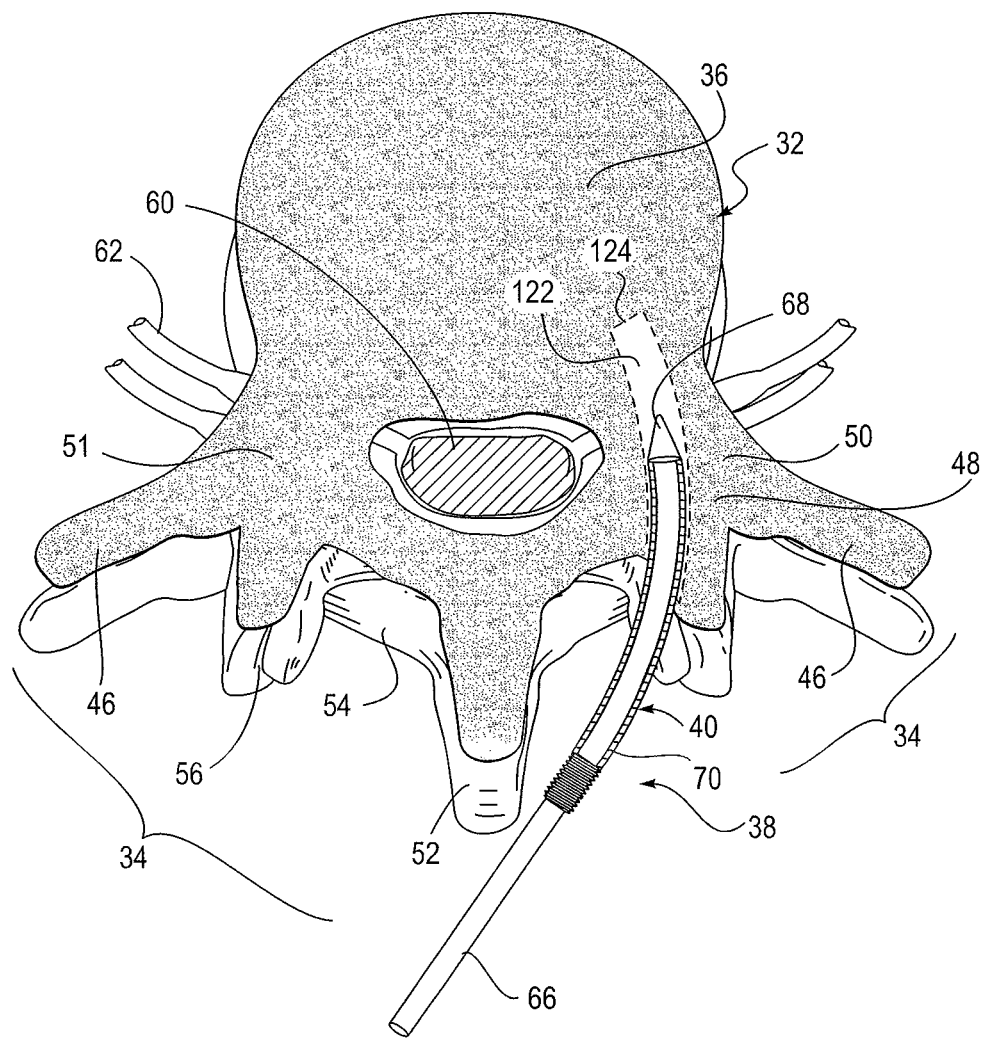
FIG. 5 is an elevational view showing positioning of the elongate member of FIG. 4, inserted into the vertebra to a second position anterior of the first position of FIG. 4.
Figure 6:
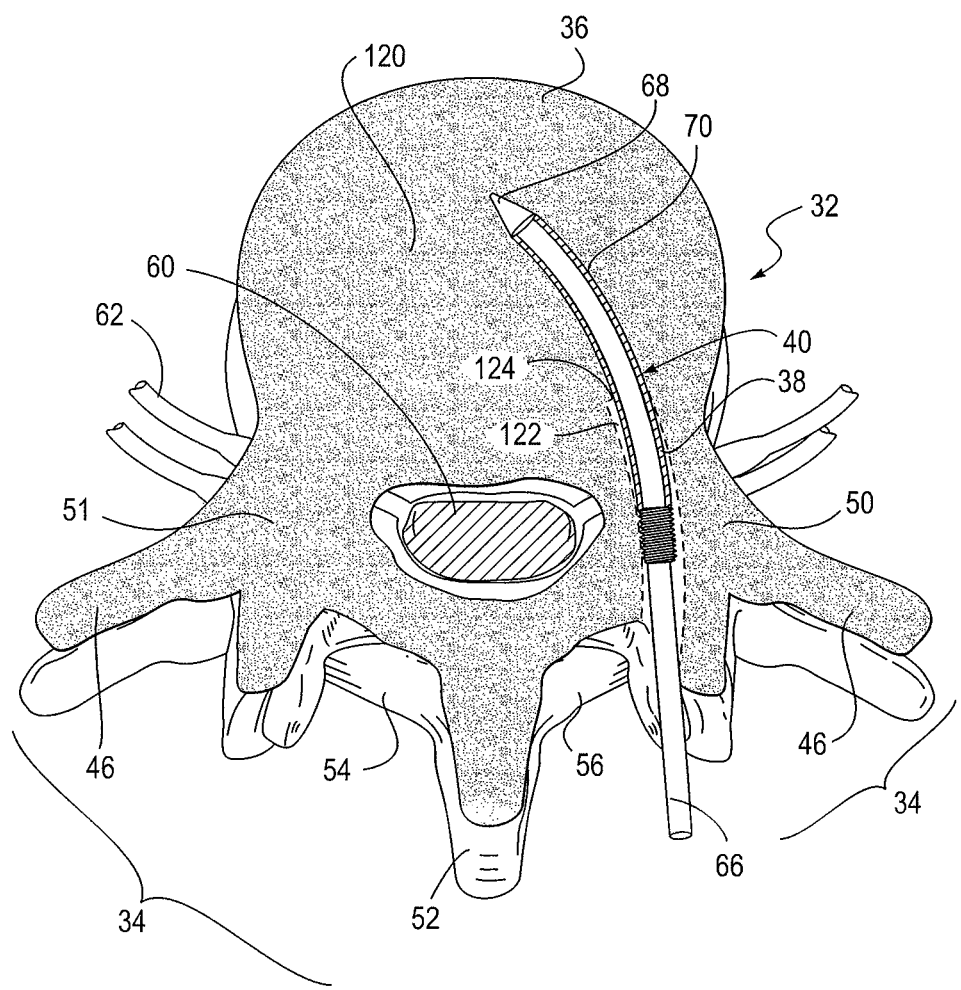
FIG. 6 is an elevational view showing positioning of the elongate member of FIG. 4, inserted into the vertebra to a third inserted position anterior of the second position of FIG. 5.

Continued insertion of the curved assembly occurs by moving the assembly 38 from the first position to a second or fully inserted position, as illustrated in the progression of FIGS. 4-6. In order to insert the posterior spinal fastener 30 further into the palpated channel 122, the physician preferably attaches an insertion tool (not shown) to the posterior end 66 of the elongate body 64 which allows the physician to move the curved assembly into the vertebra 32. In one embodiment, the physician may rotate the elongate body 64 about the central axis 88 and relative to the rigid curved oversleeve 70, thus causing the threaded end or tip of the elongate body 64, and specifically the head 68, or threaded head, to further pull the elongate body 64, which carries the curved oversleeve 70, into the vertebral body 36. Oversleeve 70 and head 68 may either be pushed into the bore 122, or head 68 may be rotated relative to oversleeve 70 during entry into bore 122 and therebeyond in order to move the whole fastening device in an arcuate manner into the body of the vertebral body. Preferably, the oversleeve 70 and head 68 are pushed into bore 122 slightly. Then, the head 68 is screwed within oversleeve 70 for movement therebeyond into the bore, and more preferably the screw may move beyond the bore into the body of the vertebra. This may occur, in one example, when the assembly is inserted into good density bone. Alternatively, in poor bone the entire assembly may be pushed into the bore and body of the vertebra. The elongate body 64 preferably is flexible and has a home or rest position with a straight configuration allowing bending and rotation within the rigid curved oversleeve 70, and preferably, permits the rotation of the elongate body about its central axis within the curved oversleeve without binding. As discussed, the outer cylindrical diameter of the posterior portion 66 of the non-threaded member 64 may be, for example, approximately 2.5 millimeters and thus smaller in diameter than the inner cylindrical diameter of the rigid curved oversleeve 70, which may have a diameter of approximately 3.5 millimeters. Thus, as the non-threaded member is advanced into the vertebral body 36, the straight posterior portion 66 of the inner non-threaded member 64 may advance into a threaded bore in the pedicle 50 of a larger diameter. Additionally, as discussed, the external substantially constant diameter of the rigid oversleeve 70 may be approximately equal to or greater than the internal diameter of the bore 122 created by the distal arcuate end of the gear shift in the pedicle 50. As a result, the posterior spinal fastener 30 fits tightly or snugly within the pedicle 50.

The threaded head 68 is advanced, moving the curved assembly into the inserted position. Preferably, the threaded head 68 is inserted beyond the arcuate bore or channel 122 created by the gear shift, thereby securely embedding the anterior portion 40 or end of the elongate member 38 in the vertebral body 36.

In an alternative embodiment, the anterior end 86 of the inner elongate body 64 may include a non-threaded head. Insertion occurs substantially as described with regard to the threaded head. However, during the insertion procedure, instead of threading the screw into the bore 122 and beyond the arcuate bore created by the gear shift, the physician merely pushes the entire assembly or elongate member 38 into the arcuate bore and/or beyond the arcuate bore to embed the elongate member 38 in the vertebral body 36.

In either embodiment, the end result is that the curved assembly or elongate member 38 is inserted into the vertebral body 36, as shown in FIG. 6, such that the arcuate anterior portion 40 of the fastener is in the vertebral body 36 and the straight posterior portion 42 of the fastener in the initially formed bore 122 in the pedicle 50. Preferably, in this inserted position, at least a portion of the curved oversleeve 70 is positioned within the bore 122 initially formed by the drill and gear shift, and a portion is positioned within the vertebral body 36, and preferably a central portion 120. In addition, at least a portion of the posterior portion 66 of the elongate body 64 extends out of or near the opening formed in the pedicle 50 at the posterior elements 34 of the vertebra 32.

A threaded oversleeve 102 may also be screwed or threaded onto the posterior aspect or portion 66 of the inner elongate body 64 and advanced into the arcuate bore in the pedicle 50. Specifically, the posterior spinal fastener 30, which has an anterior portion 40 and a posterior portion 42, is threadably secured in the vertebral body 36 by threadably or rotatably inserting the posterior portion 42 within the pedicle 50 when the anterior portion 40 is disposed within the vertebral body 36. The posterior portion 42 of the spinal fastener is threadably secured within the vertebra by placing the anterior end 106 of the threaded oversleeve 102 over the posterior end 66 of the elongate body 64 such that the elongate body 64 is received within the inner bore 108 or channel of the threaded oversleeve 102.

The external threads 112 of the threaded oversleeve 102 then rotatably engage the interior wall 126 of the arcuate bore in the pedicle 50. The external threads 112 on the threaded oversleeve 102 correspond to the thread pitch formed by the threaded head 68 on the channel 122 formed in the pedicle 50 so as to not strip the newly formed threaded bore in the pedicle 50, providing a secure attachment. When the threaded oversleeve 102 is rotated, the engagement of the threads causes the threaded oversleeve 102 to advance, both over the central elongate body 64 and into the bore or channel 122 within the pedicle 50. Thus, the threaded oversleeve 102 is advanced from a first position, substantially outside of the vertebra 32, to a second fully engaged position (see FIG. 7).

When the threaded oversleeve 102 has almost fully advanced over the posterior portion 66 of the elongate body 64 and elongate member 38, the inner threads 110 at the anterior end 106 of the threaded oversleeve 102 engage the external threads 96 on the posterior portion 92 of the curved oversleeve 70. Rotation continues so that the threaded oversleeve 102 is ultimately threadably connected to the posterior portion 92 of the curved oversleeve 70. In its fully inserted position, the threaded oversleeve 102 has its anterior portion 106 and end positioned within the channel 122 formed in the pedicle 50, and a portion of its posterior end 104, which carries the spherical portion 114, extending out of the pedicle 50 and accessible from this position.

Figure 7:
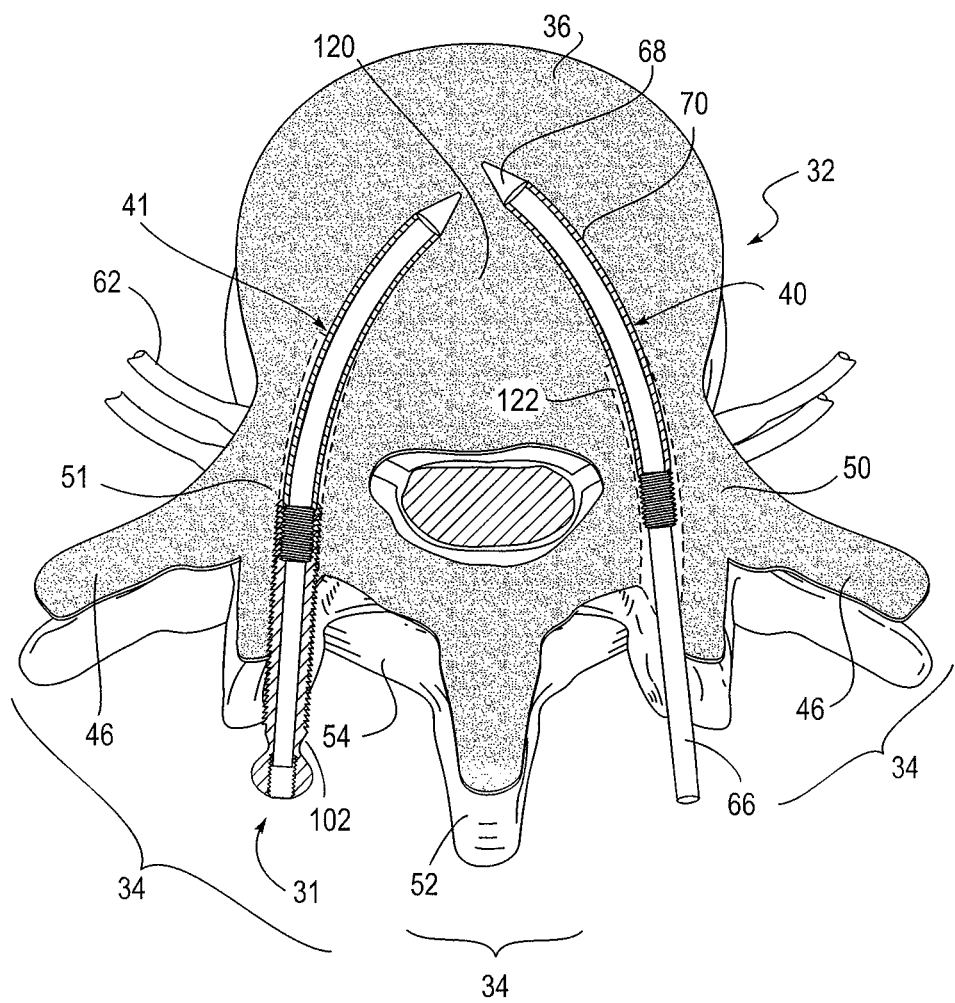
FIG. 7 is an elevational view showing positioning of the elongate member of FIG. 4, and a second posterior spinal fastener of FIG. 1 into the vertebra to a position lateral of the elongate member of FIG. 4, which devices are inserted through left and right pedicles of the vertebra.
Figure 8:
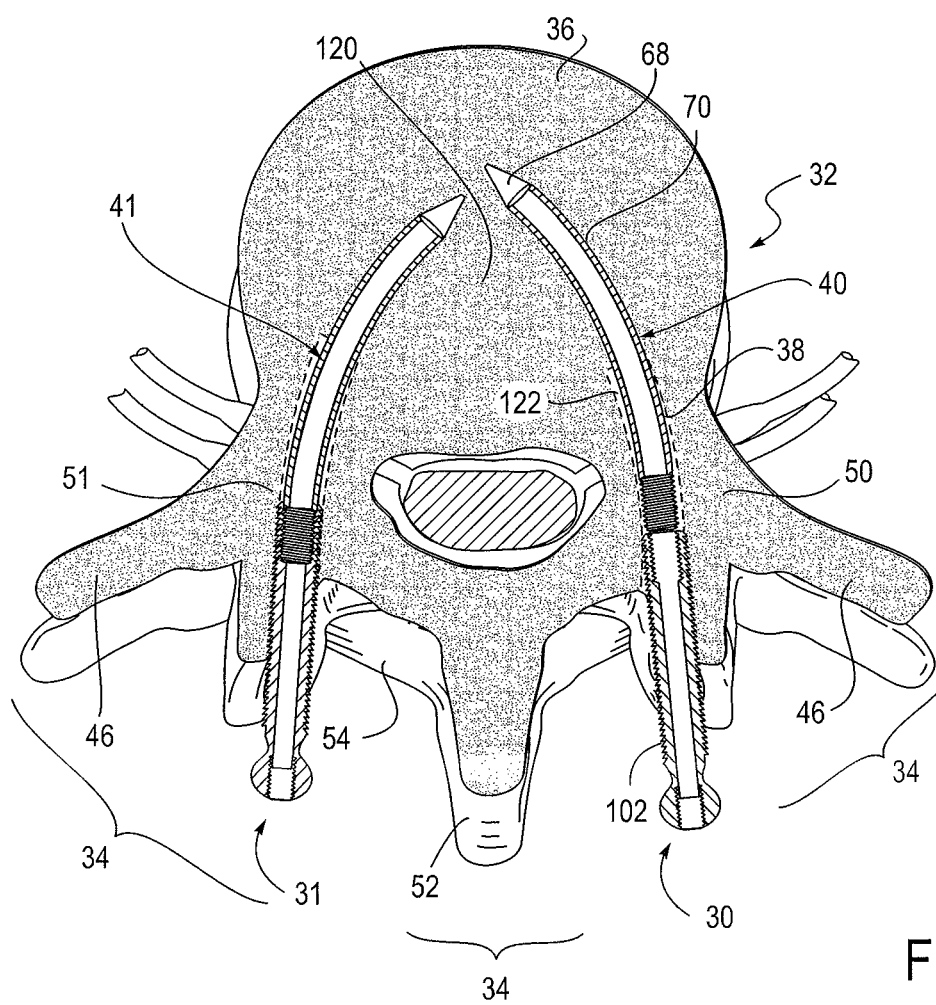
FIG. 8 is an elevational view of FIG. 7, showing the elongate member of FIG. 4, having a posterior oversleeve thereon, and the second posterior spinal fastener of FIG. 7, each inserted into the vertebra.

More than one posterior spinal fastener 30 may be inserted in a vertebra 32 using the foregoing method. For example, as illustrated in FIGS. 7-8 a first posterior spinal fastener 30 may be inserted in a right side pedicle 50 using the insertion method as described with respect to FIGS. 4-6, and a second posterior spinal fastener 30' may be inserted in a left side pedicle 51 using the same method. The first and second fasteners 30, 31 may be inserted into the pedicle 50 so that their arcuate ends 40, 41 curve toward each other.

Figure 9:
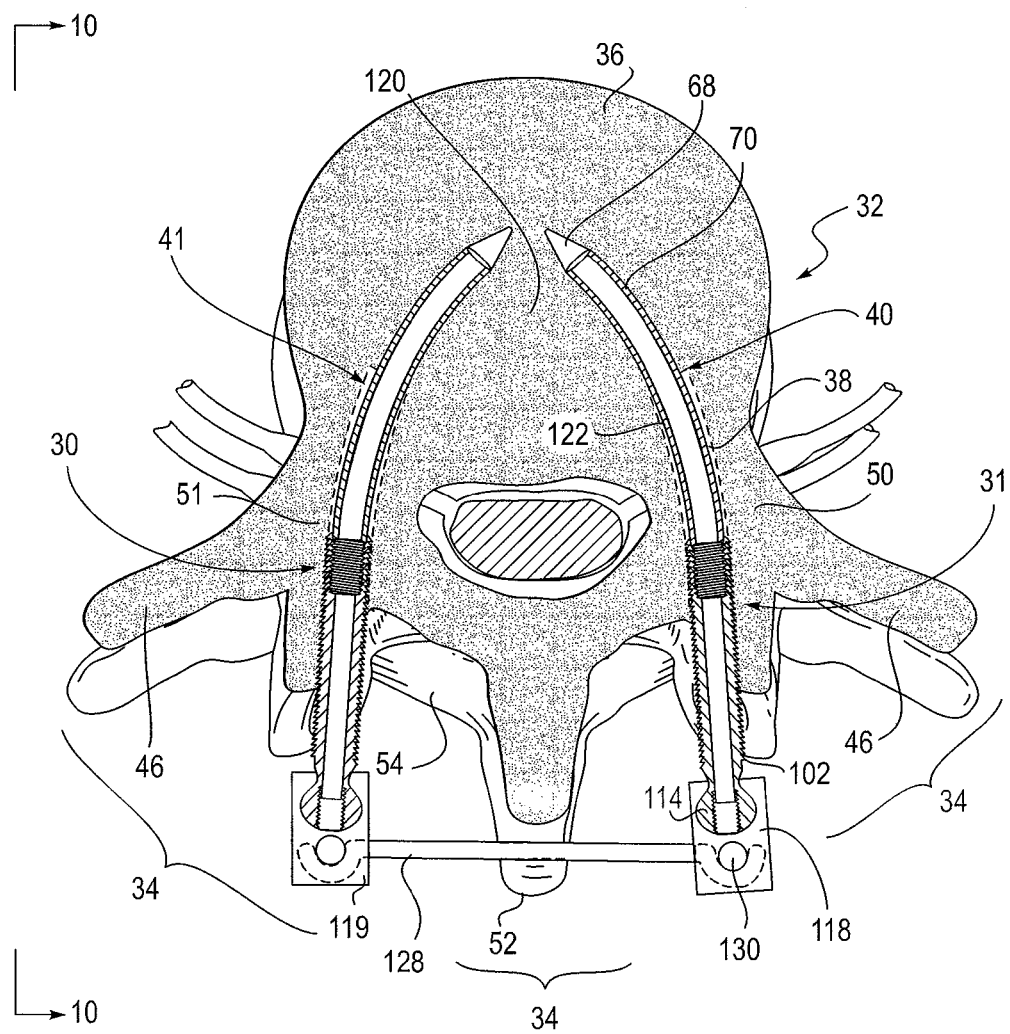
FIG. 9 is an elevational view of FIG. 8, showing a posterior spinal fastener attachment device connecting the posterior portions of the posterior spinal fasteners of FIG. 8.
Figure 10:
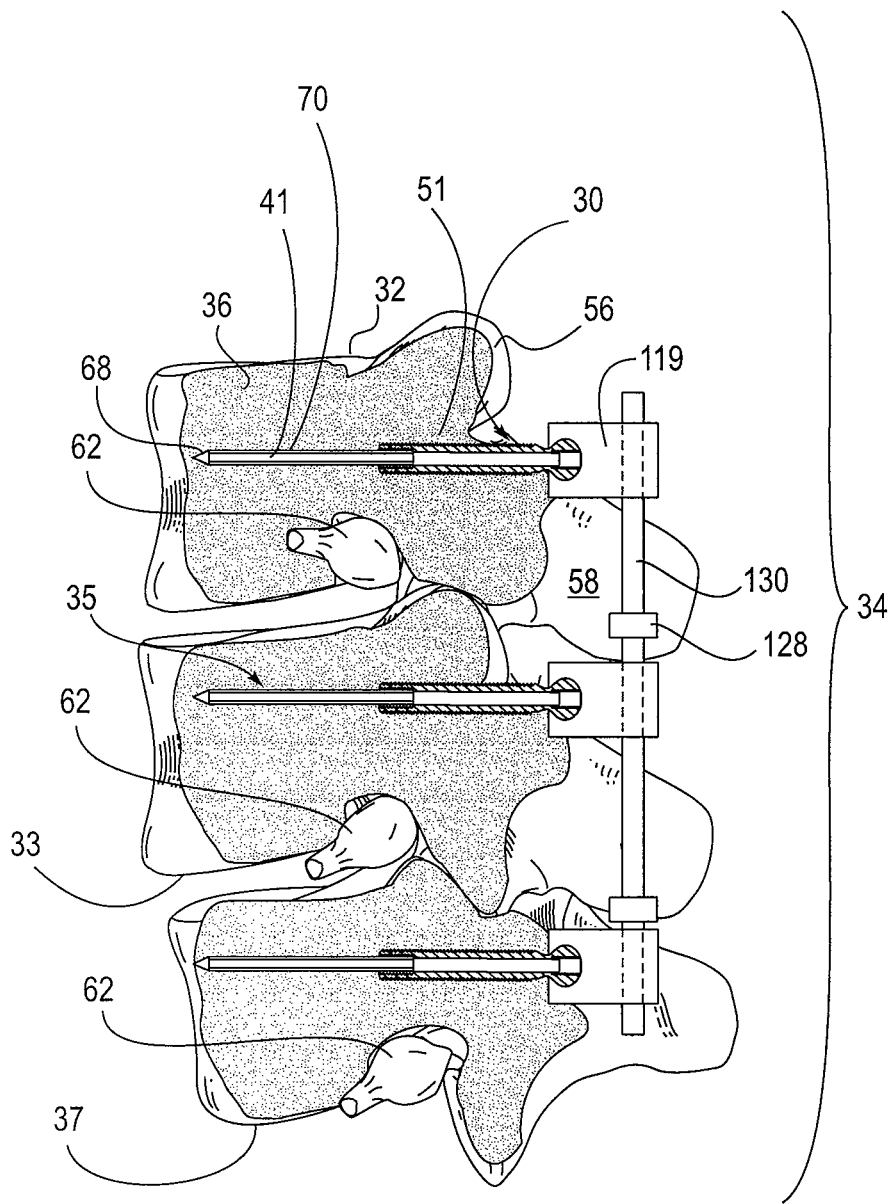
FIG. 10 is an elevational view taken along line 10-10 of FIG. 9, and showing additional posterior spinal fasteners of FIG. 1 connected in series to adjacent vertebra and interconnected by a posterior spinal fastener attachment device.

The first and second posterior or curved spinal bone fasteners 30, 31 may also be connected to each other, or to other fasteners by a variety of mechanisms known in the art. A preferred embodiment of connecting first and second fasteners includes the attachment of an anchoring member 118 to the posterior end 42 of the posterior spinal fastener 30, 31, and preferably an anchoring member which receives the spherical end 114 of the threaded oversleeve 102. A longitudinal, oblique, or transverse member 128, 130 may also be attached to the anchoring member 118. In a preferred embodiment, as is shown in FIGS. 9-10 includes the attachment of a tulip 118 as the anchoring member to the posterior end 42 of the threaded member(s) or elongate member(s) 38. Namely, the spherical head 114 of the threaded member 102 may be received in a receptor in a surface of the tulip 118. The tulip 118 may then be used to connect adjacent posterior spinal fasteners 30, 31. For instance, a cross-link 128 may engage two tulips 118 or an extension therefrom, such as a bar or rod 130 (as seen in FIG. 10) so as to connect first and second or left and right pedicular fasteners 30, 31. Adjacent vertebra 32, 33 may also be connected. For instance, a bar or rod 130 may extend from the tulip 118 on a fastener in a first vertebra 32 to a tulip 119 carried by a fastener 35 positioned in a second, adjacent vertebra 33. A third and additional vertebra 37 and left and right pedicular fasteners 30, 31 may be interconnected in this manner. The curved fastening member can also be attached to a rod or plate device via bolts, screws, slots, and/or other devices.

Figure 11:
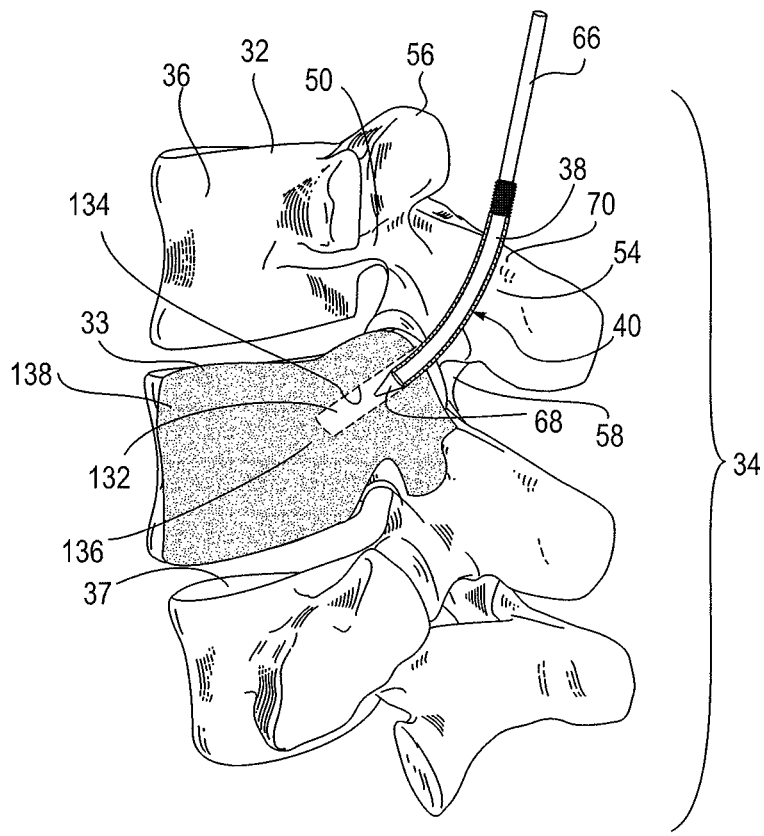
FIG. 11 is an elevational view showing positioning of an elongate member of the posterior spinal fastener of FIG. 1 in a first position for insertion into a vertebra in a laminopedicular orientation according to an alternative method of use of the posterior spinal fasteners of the present invention.
Figure 12:
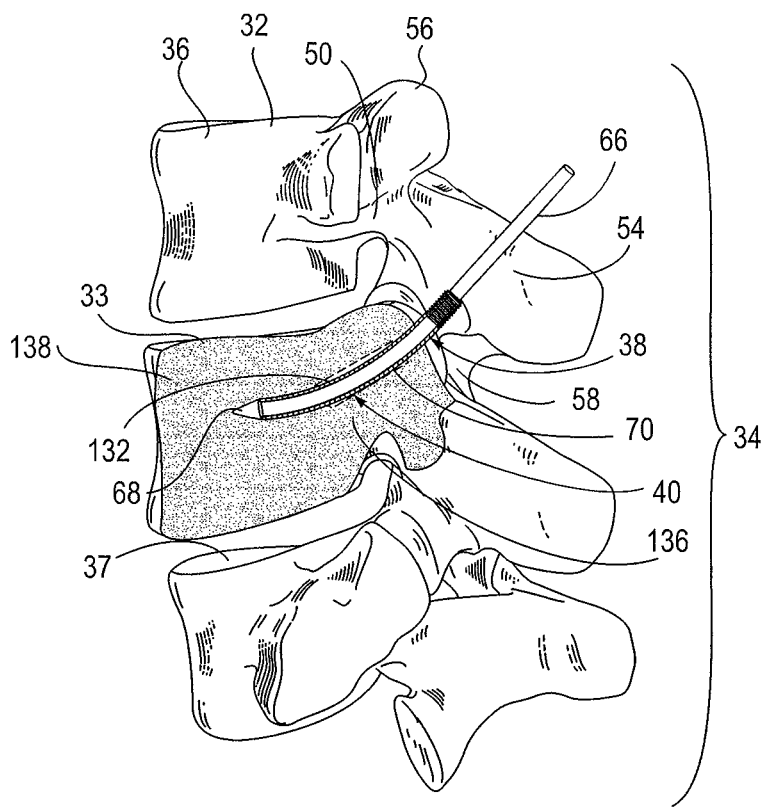
FIG. 12 is an elevational view showing positioning of the elongate member of FIG. 11, inserted into the vertebra to a second position anterior of the first position of FIG. 11.

An alternative embodiment of a method of insertion of a posterior fastening device 30 is shown in FIGS. 11-15. In the embodiment shown, the posterior spinal fastening device of FIGS. 1-3 is inserted in a lamino-pedicle, laminopedicular or transfacet orientation, in which the posterior fastening device is inserted through the lamina 54 and pedicle 136 and into the vertebral body 138. Specifically, as can be seen from FIG. 11, the elongate member 38 is inserted through the lamina 54 of a first vertebra 32 and into the pedicle 136 of an adjacent vertebra 33, so that the arcuate portion 40 of the elongate member 38 is positioned in the vertebral body 138 of the second vertebra 33, extends through the pedicle 136 of the second vertebra 33, and the straight posterior portion 42 has a portion remaining in the lamina 54 of the first vertebra 32. In the laminopedicular method, substantially as described with respect to the transpedicular embodiment described in FIGS. 4-8, and as shown in FIGS. 11-12, the lamina 54 of the first vertebra 32 is prepared for insertion, which may or may not include removing a portion of a posterior element 34 (spinous process) so as to gain access thereto. Subsequently, a drill (not shown) is used to drill a small hole through the exterior of the lamina 54 of the first vertebra 32 and into the pedicle 136 of the second vertebra 33. Then a gear shift is inserted to create an arcuate or curved bore 132 through the spongy material in the second vertebra 33 as previously described with the transpedicular insertion method.

Next the inner walls 134 of the formed channel 132 are palpated using a feeler as described to determine whether the physician has perforated the pedicle 136 of the second vertebra 33. In the preferred embodiment, the curved assembly or elongate member 38 is then inserted into the palpated channel substantially as described with respect to the embodiment of FIGS. 4-10. In the laminopedicular method, however, the elongate member 38 is moved from a first position exterior of the bore 132 into the bore formed in the lamina 54 of the first vertebra 32 and the adjacent pedicle 136 of the second vertebra 33, which bore was created by the gear shift and drill (see FIGS. 11-12). Thus during insertion, the elongate member 38 is inserted into and across the lamina 54 of the first vertebra 32 and across the pedicle 136 of the second vertebra 33 into the vertebral body 138. The elongate member 38 is inserted so as to curve inwardly toward the central portion 120 of the vertebral body 36. In its fully inserted position, the elongate member 38 is inserted into the vertebral body 138 of the second vertebra 33 as shown in FIGS. 13-15, and has its second or posterior end 42 accessible at or outside the lamina 54 of the first vertebra 32, the arcuate portion being positioned within the second vertebra 33 and the straight portion being positioned at least partially in the first vertebra 32.

The threaded oversleeve 102 may also be screwed or threaded onto the posterior aspect or portion 42 of the elongate member 38 substantially as described with respect to the embodiment of FIGS. 4-10 and advanced into the arcuate bore 132 in the lamina 54 of the first vertebra 32, pedicle 136 of the second vertebra 33 and vertebral body 138 of the second vertebra 33. Accordingly, in its fully inserted position, the threaded oversleeve 102 has its anterior end 106 positioned within the channel 132 formed in the pedicle 136 of the second vertebra 33, and its posterior end 104 having the tool engaging portion 114 extending out of the lamina 54 of the first vertebra 32 and accessible.

Figure 13:
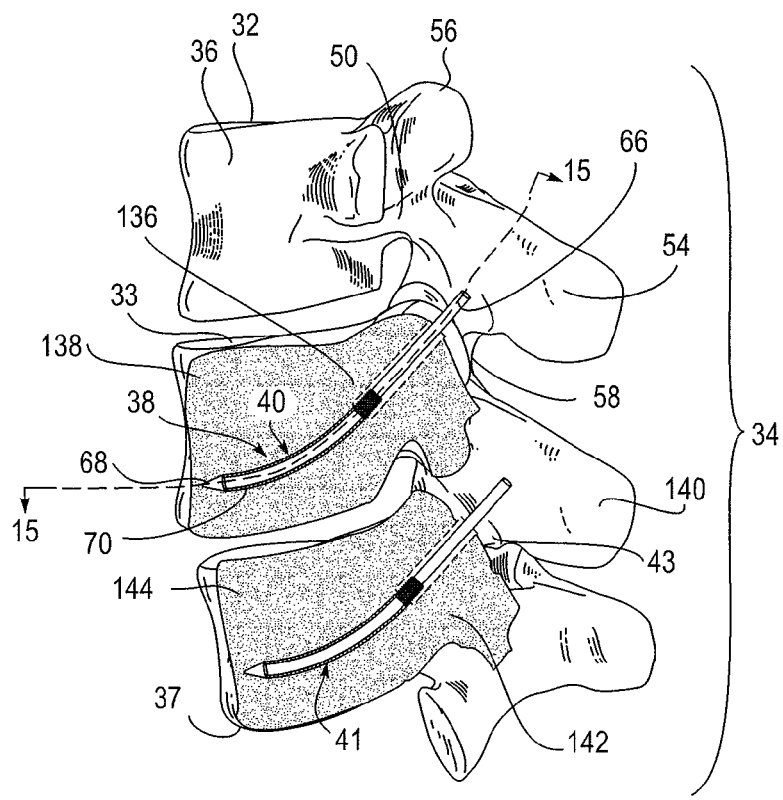
FIG. 13 is an elevational view showing positioning of the elongate member of the present invention of FIG. 12, inserted into the vertebra to a third, inserted position anterior of the second position of FIG. 12, and a second elongate member of the posterior spinal fastener of FIG. 1 inserted in parallel into an additional vertebra.
Figure 14:
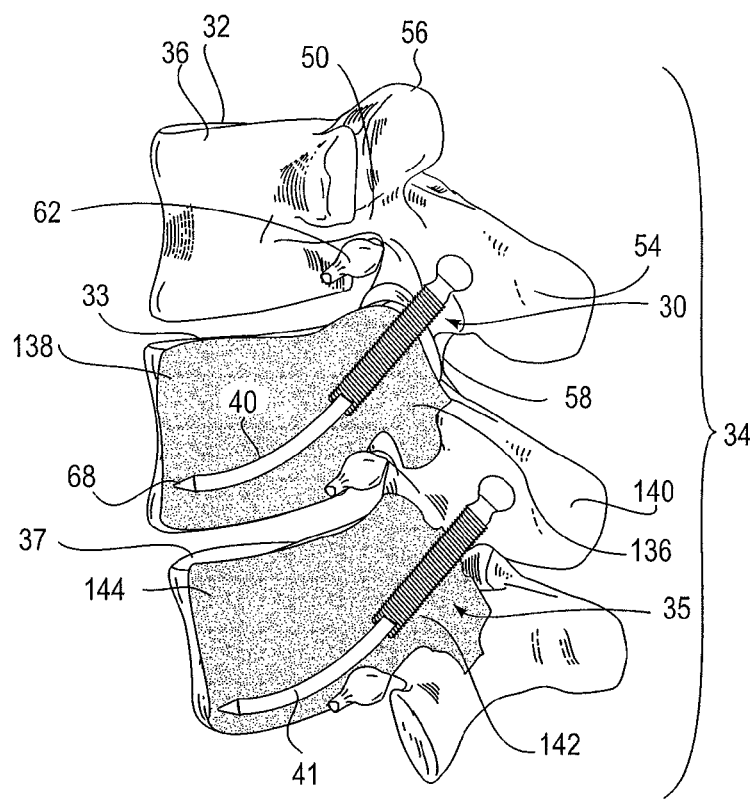
FIG. 14 is an elevational view showing the inserted elongate members of FIG. 13 having threaded oversleeves mounted thereon.
Figure 15:
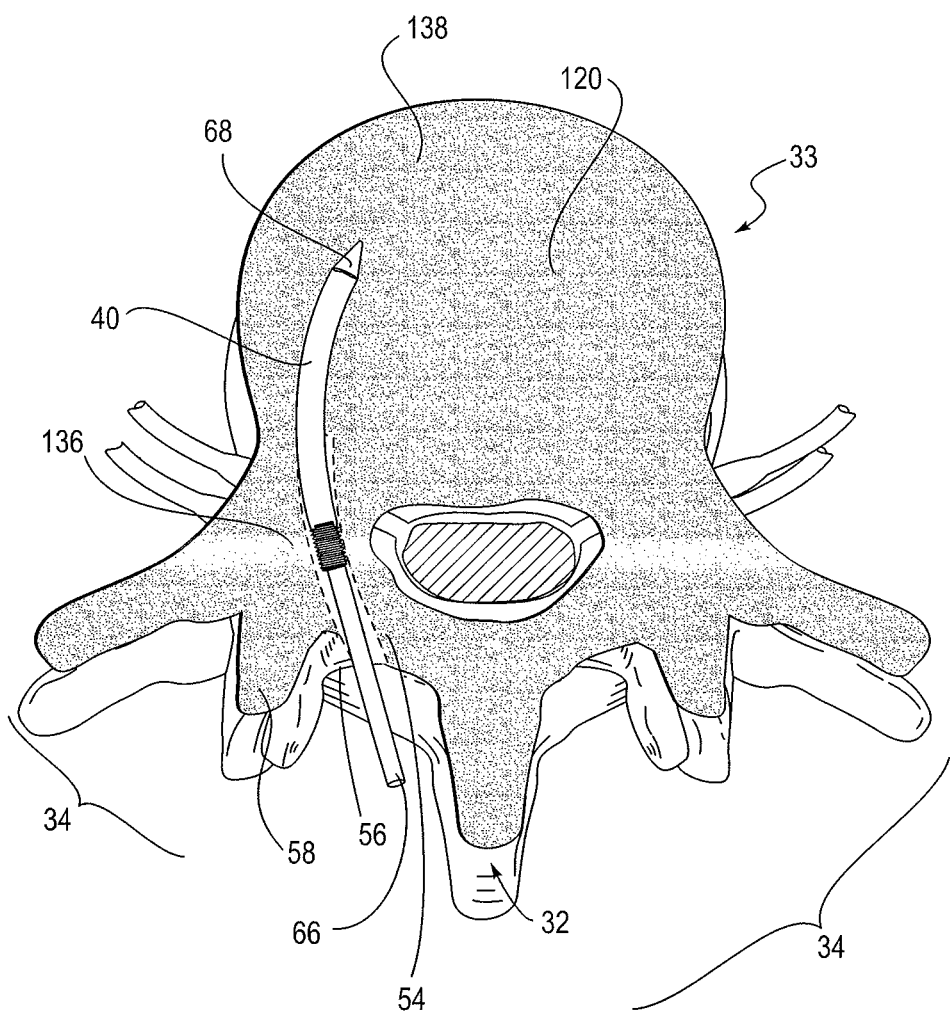
FIG. 15 is a cross-sectional view of the inserted elongate members of FIG. 13, taken along line 15-15 of FIG. 13.

Adjacent or multiple fasteners may inserted in adjacently positioned vertebra 32, 33, 37, as shown in FIGS. 13-14. The adjacent fasteners may be inserted substantially as described with respect to FIGS. 11-13. As a specific and non-limiting example, a first posterior spinal fastener 30 may be inserted across a lamina 54 of a first vertebra 32 and into a pedicle 136 and vertebral body 138 of a second vertebra 33. A second posterior spinal fastener 35 may be inserted across a lamina 140 of the second vertebra 33 and into a pedicle 142 and vertebral body 144 of a third vertebra 37. The first and second posterior spinal fasteners 30, 35 may be connected to each other, or to other fasteners by a variety of mechanisms substantially as described with respect to FIGS. 9-10.

As is known, the vertebra has a superior facet and an inferior facet forming posterior elements of the vertebra. According to an additional alternative embodiment of the method of insertion of a fastener, the fastener described with respect to FIGS. 1-3 may alternatively be extended through the superior facet for entry into the pedicle. Insertion occurs substantially as described with respect to the embodiments of FIGS. 4-15. Similar to the embodiment of FIGS. 11-15, the method of introduction includes inserting the elongate member through the superior facet of the vertebra, through the pedicle and into the vertebral body. In an alternative embodiment, the fastener may be inserted into a first vertebra by extending the fastener through the inferior facet of the first vertebra and into an superior facet and the pedicle of the second vertebra. According to a preferred embodiment, the spinous process may or may not need to be removed based on a patient's particular geometry. In the transfacet method of insertion, a small drill may be used to create an access pathway from the inferior process of the superior vertebra through the superior process of the inferior vertebra, the anatomical facet joint, and into the pedicle itself to the junction of the pedicle and the vertebral body of the inferior vertebra. After a projected pathway is created with the drill, the site is then prepared with a gearshift that fits the geometry of the anatomy and projected linear course of the fastener. The curved elongate member is geometrically configured to negotiate this entrance to the vertebral body. Accordingly, the curved spinal fastener is inserted into the bore and therebeyond as described in the method herein in relation to FIGS. 4-6. After reaching the base of the pedicle and extending a small distance beyond the base of the pedicle, preferably a distance ranging from three to 15 millimeters, the curved assembly begins its geometrical match to vertebral body curvature, progressively heading in a medial direction.

The foregoing described geometry greatly enhances the pullout strength of the assembly. In addition, the fastener assembly may provide for different degrees of curvature, allowing for a more gradual bend towards the center of the vertebra on one side and a more radical and shorter final placement in the vertebra from the opposite side. This facilitates technical variation in "medialization" or "centralization" of the fasteners in different depths of the vertebral body.

The present invention and method have several advantages over traditional pedicle screws. A curved fastener or post is provided that can be inserted as either a transpedicular, transfacet, or a laminopedicular fastening device that improves stability without relying on pullout strength of the screw. The diameter of the posterior fastening device 30, or screw, of the present invention may be less than the external diameter of currently used screws. As a result, there is less risk that the posterior fastening device will penetrate the sidewall of the pedicle 50 and contact a nerve. In addition, since the posterior fastening device is curved or has an arcuate portion which is positioned within the vertebral body 36, it is not directly dependent upon the density of the bone as related to the pullout strength of the screw, which relies on the threads of the conventional pedicle screw. Instead, the pullout force it is related more to overcoming a compressive force applied to the bone within the vertebral body by the curved member within the vertebral body 36. Thus, instead of being susceptible to a sheer force which may pull the screw out, the posterior fastening device of the embodiment described requires a compressive force in order to pull the device out. As is known, bone is much stronger in compression than in sheer. Thus, the present invention replaces former sheer pullout forces of traditional pedicle screws with compression pullout forces to take advantage of the bone strength in compression. In other words, the curved anterior end of the screw will not pullout directly, as it will engage tissue when such force is applied. Advantageously, when a plurality of posterior fastening devices are connected together, as for example one fastening device on each side of the vertebra 32 or one fastening device on the left pedicle 50 and one on the right pedicle 51, the combined fastening devices form a "claw" within the vertebral body 36. As a result, in order for the claw to be pulled out, all the bone within the vertebral body 36 must be compressed. Furthermore, each of the posterior ends of the screws are rigidly connected to each other at the posterior end, and therefore they cannot bend or move back along the insertion path as they are pulled out. The invention further utilizes external threads on the threaded oversleeve 102 which operate like a standard pedicle screw and add to the pullout resistance force caused by those threads engaging the inner portion of the pedicle 50.

The curved pedicle screw assembly or elongate member according to an alternative embodiment, shown in FIGS. 16-17, is formed by a rigid elongate member 230 having a shaft with a straight posterior portion 232 and an arcuate anterior portion 234. In this alternative embodiment, the rigid curved oversleeve and rigid elongate body of the embodiment of FIGS. 1-3 may be one member, that is one unitary or integral rigid member. The unitary member preferably has a length ranging from 10 to 300 millimeters, and more preferably 20 to 150 millimeters.

The anterior portion 234 of the rigid member 230 is arcuate or curved in shape, and extends from an interior portion 236 of the rigid member 230 to an anterior end 238 of the rigid member 230. The anterior portion has a length ranging from five to 200 millimeters and more preferably from ten to 30 millimeters. The radius of curvature of the anterior portion 234 can range from two millimeters to four meters, and more preferably from ten millimeters to two meters. The radius of curvature may or may not be uniform throughout the length of the curved portion of the fastening device. Preferably, a portion or all of the outer surface 240 of the shaft of the anterior portion 234, which is preferably cylindrical, is smooth or may include a roughened surface. The diameter of the shaft of the anterior portion 234 of the rigid member 230 is preferably wider than the diameter of the shaft of the posterior portion 232. The diameter of the substantially cylindrical anterior portion ranges from one to 20 millimeters and more preferably from two to ten millimeters.

A head 242 is carried by the anterior end, and may be rounded or have a conical shape, which decreases in diameter toward a distal tip. The head 242 has an outer diameter, or maximum diameter which is preferably approximately equal to the outer cylindrical diameter of the shaft of anterior portion 234 of the rigid member 230. Thus, the tip or head 242 of the rigid member 230 of the fastener 230 has a diameter at its widest point that is the same as the diameter of the fastener 230 but tapers either conically, with or without threads, bluntly, spherically, or in any other shape that may be suitable for insertion. The head 242 may be composed of a substantially smooth or roughened surface.

The posterior portion 232 of the fastener or post or shaft of the rigid member 230 is straight, or extends in a linear direction, and preferably extends from the interior portion 236 of the rigid member 230 to a posterior end 244 of the rigid member 230. The length of the posterior portion 232 can range from five to 100 millimeters and more preferably from ten to 45 millimeters. The posterior portion 232 may have an outer cylindrical surface having a diameter which, as described above, is narrower than the outer surface diameter of the anterior portion 234. In particular, the outer diameter of the posterior portion 232 ranges from one to 20 millimeters and more preferably ranges from two to 15 millimeters and is even more preferably approximately 2.5 millimeters. The outer surface 246 of the posterior portion 232 may be smooth or threaded or may include a roughened surface along at least a portion thereof.

The interior portion or neck 236 of the rigid elongate member 230 is spaced a distance from the ends 238, 244 of the member, and has an outer thread 248 surrounding at least a portion thereof. In addition to the external thread 248, the interior portion 236 may have a varying outer diameter. Specifically, the interior portion, which connects the anterior portion 234 and posterior portion 232 of the rigid oversleeve, may include a first diameter which is preferably a maximum diameter corresponding with the approximate diameter of the anterior portion 234 and a second diameter, which is preferably a minimum diameter, which corresponds with the approximate diameter of the posterior portion 232. More specifically, the interior portions is tapered, or conical in shape, and in this regard the outer diameter of the interior portion narrows from the first diameter to the second diameter.

The rigid member 230 may be formed of a solid material, and in one embodiment includes a cylindrical cross-section, and has a surface 40, 46 which may be smooth or roughened for bone in growth. The material used may be titanium, stainless steel or any other material suitable for fixation of the spine. The material used may also resorb or may not resorb.

A threaded oversleeve 102, substantially as described with respect to the embodiment of FIGS. 1-3, may also be screwed or removeably threaded onto the posterior aspect or portion 232 of the rigid member 230. More specifically, in the present embodiment the posterior portion 232 of the rigid member 230 may carry the threaded oversleeve 102. The threaded oversleeve 102 thus has a centralized bore 108 extending along its length which, preferably, has an inner diameter corresponding to the outer diameter of the posterior portion of the rigid member 230. The bore 108 is, therefore, adapted to receive the rigid member 230. The threaded oversleeve 102 also preferably has an inner thread 110 at its anterior end 106 that is adapted for engaging the external thread 248 on the interior portion 236 of the rigid member 230 so as to permit the threaded oversleeve 102 to be removeably secured to the rigid member 230. While a threaded oversleeve 102 is described hereinabove, the rigid curved pedicle fastener 230 may be used without a threaded oversleeve 102.

The insertion and use of the rigid fastener 230 is substantially similar to that set forth with regard to the embodiment of FIGS. 4-15. Thus, the elongate rigid member 230 may be inserted in the transpedicular, laminopedicular or transfacet orientation substantially as described. However, because the present embodiment of FIGS. 16-17 is a curved rigid member, the anterior end 238 of this alternate embodiment preferably carries a non-threaded head 242. Accordingly, during the insertion procedure, instead of threading a screw-type head and anterior portion of the elongate member beyond the arcuate bore, the physician merely pushes the entire rigid elongate member 230 into the arcuate bore 122 in the vertebra 32 and posterior elements 34, and more specifically pushes the member further beyond the arcuate bore in the pedicle 50 to embed the posterior end 232, 244 in the vertebral body 36. The end result is that the single rigid member 230 is inserted into the vertebral body 36 such that the arcuate anterior portion 234 of the rigid fastener is located in the vertebral body 36 and the straight portion or the posterior portion 232 is located in the initially formed bore 122 in the pedicle 50, and accessible at its posterior end substantially as described with regard to the embodiments of FIGS. 4-15.

Multiple rigid fasteners may be inserted and interconnected as previously described with respect to the first embodiment.

Similar to the embodiment of FIGS. 1-15, the rigid fastener 230 and method of insertion or use thereof have several advantages over traditional pedicle screws. Namely, the diameter of the posterior fastening device of the present invention is less than the external diameter of currently used screws. Thus, there is less risk that the posterior fastening device will penetrate the sidewall of the pedicle 50 and contact the nerve. The rigid posterior fastening device 230, likewise, has a curved or an arcuate portion which is positioned within the vertebral body 36, and therefore, instead of being susceptible to a sheer force which may pull the screw out, the posterior fastening device of the embodiment described requires a compressive force in order to pull the device out. Likewise, when a plurality of posterior fastening devices are connected together, as for example one fastening device on each side of the vertebra 32 or one fastening device on the left pedicle 50 and one on the right pedicle 51, the combined fastening devices form a "claw" within the vertebral body 36. Furthermore, each of the posterior ends of multiple rigid members may be rigidly connected to each other at the posterior end, and therefore they cannot bend as they are pulled out. Also, as with the prior embodiment, the invention further utilizes external threads on the threaded oversleeve 102 which when used, adds to the pullout resistance force caused by those threads engaging the inner portion of the pedicle 50.

The curved posterior spinal fastener 330 or elongate member according to an alternative embodiment, shown in FIGS. 18-19, may be cannulated. More specifically, the elongate member 332 of the posterior spinal fastener is provided with a passageway or bore 334 extending longitudinally therethrough. The elongate or cannulated member may be formed by a rigid or elastic or partially flexible material having a straight posterior portion 336 and an arcuate anterior portion 338. The cannulated member 332 may or may not be fenestrated.

The elastic cannulated elongate member 332 may have an elastic elongate body 340 containing the elongate or longitudinally extending bore 334, and a rigid curved oversleeve 70 (not shown). The elastic cannulated elongate member 332 has a length which can range from five to 200 millimeters, and more preferably from 20 to 60 millimeters. Similar to the embodiment of FIGS. 1-3, the anterior portion 342 of the inner elongate cannulated body 340 extends from an interior portion 344 of elongate body 340 which is spaced a distance from the posterior end 346 and anterior end 348 of the elongate body 340. The anterior portion 342 has a length ranging from five to 100 millimeters, and more preferably from ten to 30 millimeters. The outer surface 350 of the elongate body 340 at its anterior portion 142 is preferably cylindrical and may be smooth or threaded or may include a roughened surface along at least a portion thereof. The outer diameter of the substantially cylindrical shaft of the elongate body 340 can range from one to 25 millimeters and more preferably from two to 15 millimeters. The centralized bore 334 has a cylindrical cross-section and extends the length of the member from the posterior end 346 to the anterior end 348 of the elongate body 340. The cylindrical inner diameter of the centralized bore can range from 1 mm to 25 mm, and more preferably from 1.5 mm to 14 mm. In this embodiment, the elongate body 340 is preferably elastic, or flexible along a portion thereof, and more preferably, the shaft is flexible along at least its anterior portion 42 so as to bend and become arcuate in shape by the attachment of a curved oversleeve 70 substantially as described with respect to the embodiment of FIGS. 1-3. The elongate cannulated body 340 may thus be formed of a material such as a shape memory material or alloy. However, a non-memory material or alloy such as titanium, stainless steel, or any other material suitable for fixation of the spine may also be used. The material used may also resorb or may not resorb. The anterior portion 342, as indicated, is carried within curved oversleeve 70. To this end, curved oversleeve 70 may be a threaded oversleeve having a centralized bore 108 extending along its length which, preferably, has an inner diameter corresponding to the outer diameter of the posterior portion of the rigid member 230. The bore 108 is, therefore, adapted to receive the anterior portion 342. The inner thread 110 at the anterior end 106 may engage an external thread 343 on the member 342 so as to permit the threaded oversleeve 102 to be removeably secured.

As can be seen in FIG. 18, the posterior portion 336 of the cannulated elongate body 340 extends from an interior portion 344 of the elongate body 340 to a posterior end 346.

Preferably, the posterior portion 336 has a length ranging from five to 100 millimeters and more preferably from ten to 30 millimeters. The posterior portion 336 has an outer diameter formed by an outer cylindrical surface which may be the equivalent of or different from the outer diameter of the anterior portion 342 of the elongate body 340. To this end, the outer diameter of the posterior portion 336 can range from one to 25 millimeters and more preferably from two to 15 millimeters. Additionally, the outer surface 352 of the posterior portion 336 may be smooth or threaded or may include a roughened surface along at least a portion thereof.

Preferably, the posterior portion 336 of the elongate body 340 has an end provided with a threaded or smooth connector that may either attach on the outside or on the inside be adapted to receive, for example, a syringe 366. Syringe may have an end which is smooth or alternatively may include a thread, and can thus provide an interference fit or be screwed onto the end of the elongate member 332 by connection to the connector, or directly to the posterior portion. The introducing device or syringe 366 has a corresponding opening which is, thus, placed in communication with the centralized bore 334 of the cannulated body 340 for transmission of the solidifying agent 364 or any suitable material into and through the elongate cannulated member.

Alternatively, the entire combination of the elongate cannulated member, namely the elongate body 340 and curved oversleeve 70, may be a rigid single device as shown in FIGS. 18-19, substantially as described with respect to the embodiment of FIGS. 16-17. However, the rigid cannulated member may include a centralized bore extending the length of the member from the posterior end to the anterior end.

Each of the foregoing elongate cannulated members may carry a threaded oversleeve 102, substantially as described with respect to the embodiments of FIGS. 1-3 and 16-17, which is preferably carried or threadably attached onto the posterior aspect or portion 336 of the elongate member 332. While a threaded oversleeve 102 is described, the elongate cannulated member may be used without a threaded oversleeve 102.

One or more apertures 356, such as bores, pores, fenestrations, slots, and/or slits, may optionally be provided in the fastener or post. Preferably, the anterior portion 338 of the cannulated member is fenestrated. A plurality of apertures or fenestrations 356 may be positioned along the shaft of the cannulated member 332 and may be spaced longitudinally and/or circumferentially as desired. Additionally, a cannulated elongate member 332 may include one or more apertures 356 in the periphery permitting the insertion of an appendage, such as an arrow-like appendage for further anchoring the fastening member in the vertebral body 36. For instance, the appendage may be provided for insertion through the cannulated bore, wherein the arrow-like projections face posteriorly, so that, when the appendage is inserted and then pulled back, it deploys the arrows out of the fenestrations. In another alternative embodiment, a mesh or net may be inserted through the cannulated bore that is deployed into the vertebral body and then the solidifying agent is inserted. The mesh may be used to strengthen the solidifying agent.

As shown in FIG. 19, in a preferred embodiment, the centralized bore 334 of the cannulated member is adapted to receive a stylet 358 or similar device such as a rod, nail, spike or screw therein which has an anterior end including a tip 360 thereon and a posterior end having a stop or flange 362. Preferably, the stylet 358 has an outer cylindrical surface with an outer diameter sized to fit within the centralized bore 334 of the cannulated member, and therefore preferably has a diameter of ranging from 0.1 mm to 24 mm and more preferably from 1 mm to 15 mm. The stylet 358 has a length greater than that of the cannulated member 332, so that the anterior tip 360 extends beyond the anterior end 348 of the cannulated member and the head 362 is positioned adjacent to or abuts the posterior end 346 of the cannulated member. Preferably, the length of stylet 358 can range from five to 300 millimeters and more preferably from ten to 200 millimeters. It is contemplated that the anterior tip 360 may include an external thread for use in threaded insertion of the assembly. The flange 362 preferably has an outer diameter which is larger than the inner diameter of the centralized bore 334 of the cannulated member, so that the flange 362 serves as a stop, preventing further insertion of the stylet 358 into the cannulated member 332. To this end, the flange 362 has an outer diameter ranging from two to 30 millimeters and more preferably from three to 20 millimeters. The stylet 358 may comprise a material suitable for use in the mammalian body, and preferably a flexible or elastic material, so as to permit introduction through and removal from the curved anterior portion 338 of the cannulated member without binding.

Figure 20:
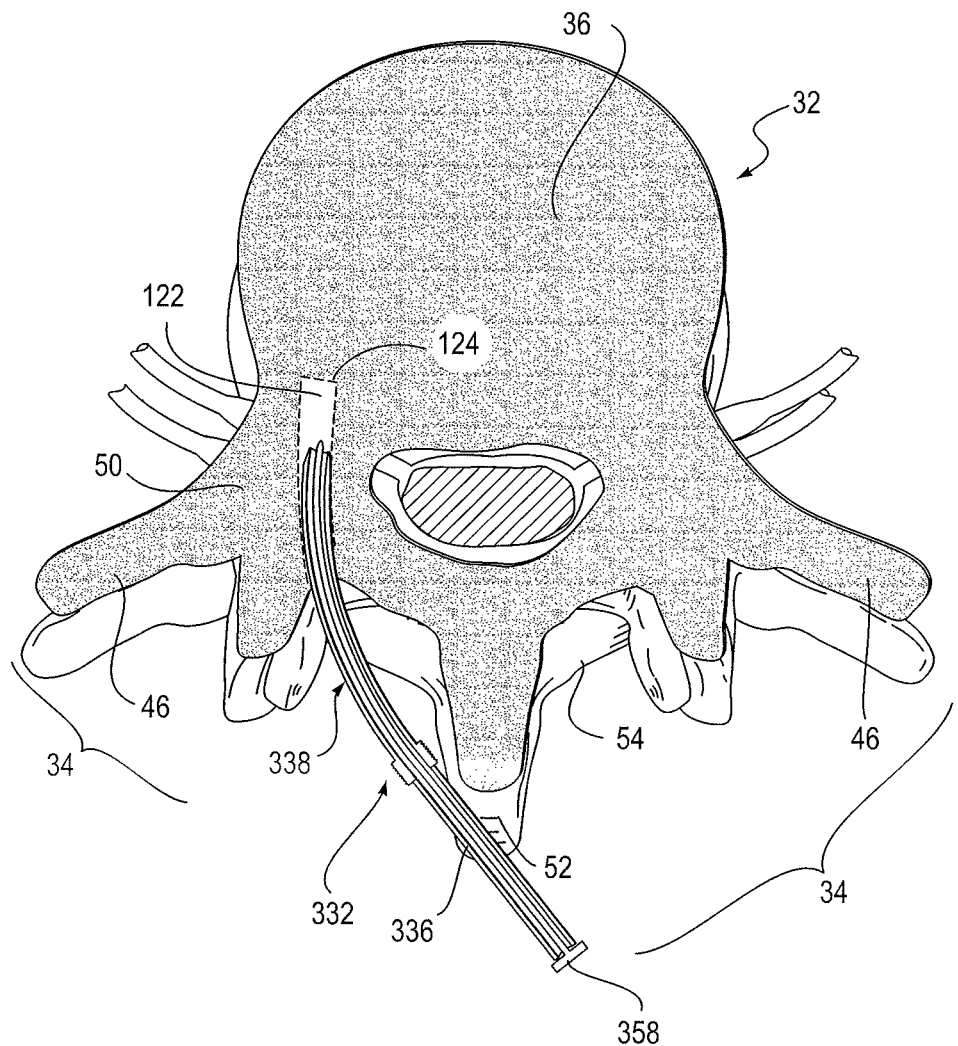
FIG. 20 is an elevational view showing positioning of an elongate member and stylet of FIG. 19 in a first position for transpedicular insertion into a vertebra according to a method of use of the posterior spinal fastener.
Figure 21:
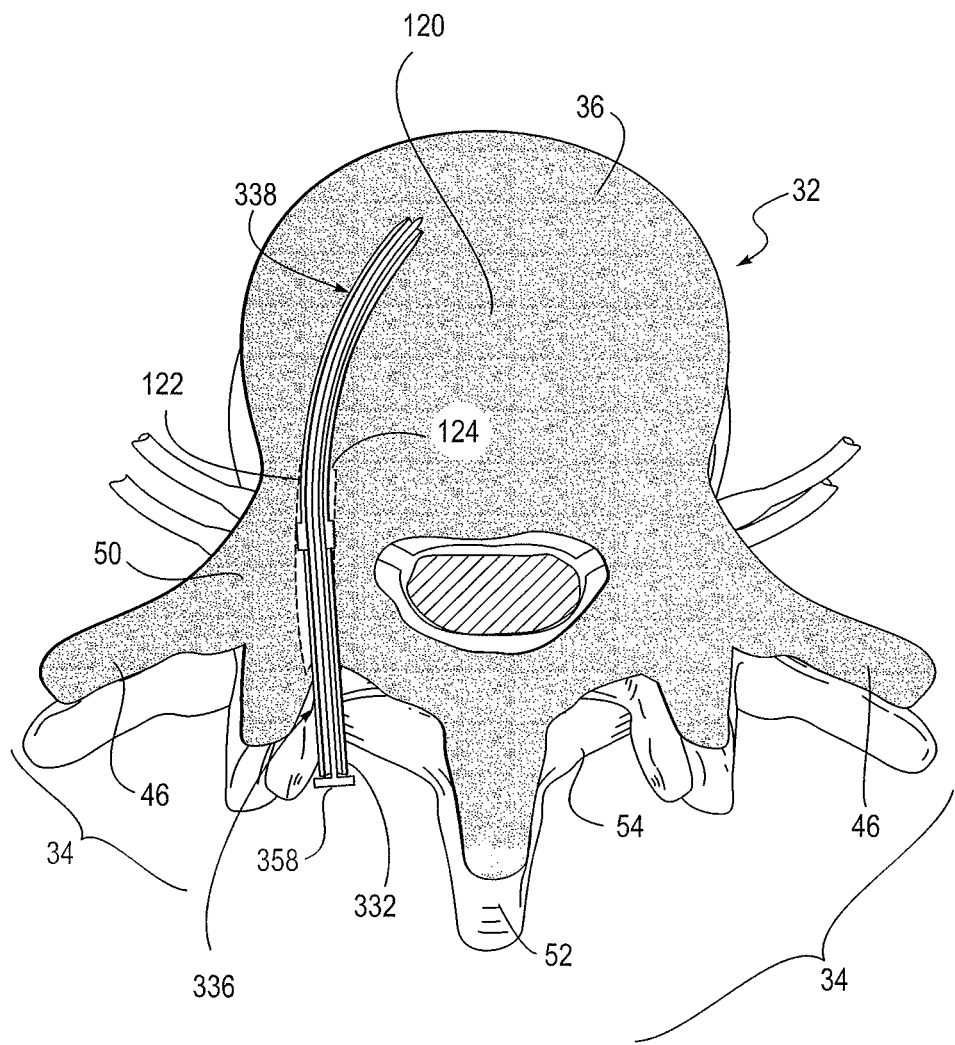
FIG. 21 is an elevational view showing positioning of the elongate member and stylet of FIG. 20 inserted into the vertebra to a second, inserted position anterior of the first position of FIG. 20.
Figure 22:
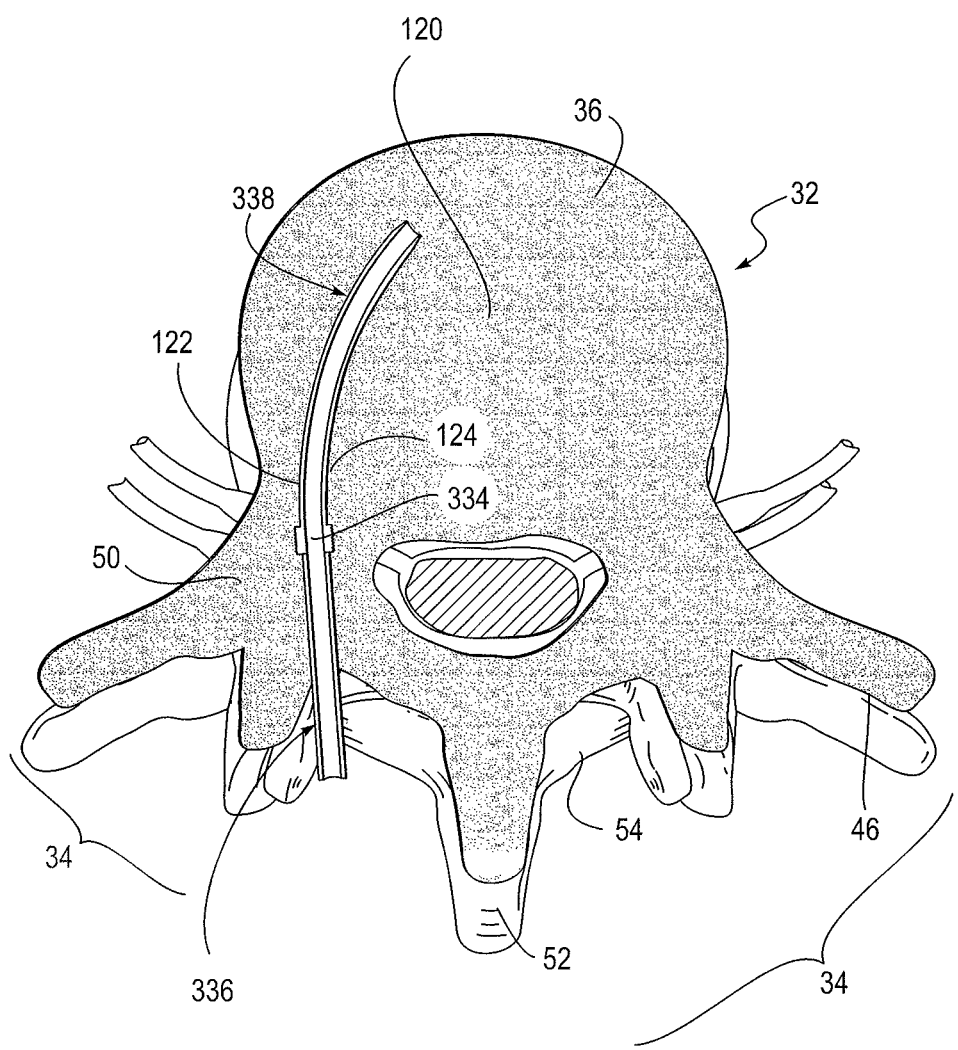
FIG. 22 is an elevational view showing positioning of the elongate member of FIG. 21, with stylet removed as shown in the elongate member of FIG. 18.

A preferred method of use of the posterior spinal fastener, or cannulated elongate member 332 described in FIGS. 18-19, is described in reference to FIGS. 20-22, which illustrate insertion in a transpedicular orientation. It is noted that FIGS. 20-28 are schematic in that the central bore and/or stylet are visible through the elongate member and/or oversleeve. Accordingly, the posterior spinal fastener 330 is inserted substantially as described with respect to FIGS. 4-8. However, in the method of use of the cannulated elongate assembly 330, the stylet 358 is first inserted into bore 334 of the cannulated elongate member 332 prior to insertion into the pedicle 50. The combined cannulated member 332 and stylet 358 forms the elongate member which is then inserted substantially as described hereinabove, moving the assembly from a first position (not shown) in which the cannulated member 332 is initially inserted into the verterba, to a second or fully inserted position, illustrated in FIG. 21. As with the previously described embodiment, in the inserted position, the anterior end 348 is inserted beyond the arcuate bore or channel 122 created in the pedicle 50, thereby securely embedding the end of the spinal fastener 330 in the vertebra 32. The removable threaded oversleeve 102 may also be optionally attached as described with respect to the embodiment of FIGS. 4-15.

In this position, the cannulated assembly is positioned in the vertebral body 36, as shown in FIG. 21, such that the arcuate anterior portion 338 of the fastener is in the vertebral body 36 and the straight portion 336 of the fastener in the initially formed bore 122 in the pedicle 50. Preferably, in this inserted position, at least a portion of the curved portion 338 is positioned within the initially formed bore 122 and a portion is positioned within the vertebral body 36. In addition, at least a portion of the posterior portion 336 of the elongate member 332 extends out of or near the opening formed in the pedicle 50, and thus the elongate cannulated member and bore 334 therein is accessible from outside of the vertebral body 36. Preferably, the vertebral portion into which the posterior spinal fastener 30 is inserted has a radius in cross section and a central portion 120 of the vertebra has a radius in cross section that is not greater than three-quarters (¾) times the radius of the vertebral portion. More preferably, the radius of the central portion 120 is not greater than two-thirds (⅔) times the radius of the vertebral portion. Even more preferably, the radius of the central portion 120 is not greater than one-third (⅓) times the radius of the vertebral portion and may even be as narrow as one-quarter (¼) times the radius of the vertebral portion.

While a method of insertion by means of transpedicular insertion is specifically described, the elongate cannulated member may also be inserted in the laminopedicular or transfacet orientations in the manners substantially as described herein.

Once the cannulated assembly is in its inserted position, the stylet 358 is removed from the elongate cannulated member (see FIG. 22), so that bore 334 forms a channel into the interior of the vertebral body 36.

Following the insertion of the cannulated assembly and removal of stylet 358, a syringe or reservoir, or delivery device is loaded with material for delivery into the vertebra. Acceptable introducing devices include a syringe, nozzle, reservoir, or any delivery device suitable for the purposes provided. Any suitable technique may be utilized for delivering the material, including pressurization using a hydraulic syringe, vibration, manual pressure or a combination of any of the foregoing.

Specifically, the syringe or reservoir, or delivery device may be loaded with a bone fastening cement, antibiotics, bone healing compounds, a mesh device or other materials that may help in the reconstruction of the anatomy of the spine, may help in structural stability, may help in decreasing the rate of infection, and/or may help in healing of the spine. As a non-limiting example, a solidifying material or agent 364 may be loaded into the syringe for introduction into the vertebra 32, to inhibit unwanted pullout of the posterior spinal fastener, such as but not limited to a solidifying agent 364. Acceptable solidifying agents include bone cements, calcium sulphates, calcium phosphates, polymethylmethacrilates, or any other suitable absorbable or non-absorbable agent available from multiple manufacturers.

Figure 23:
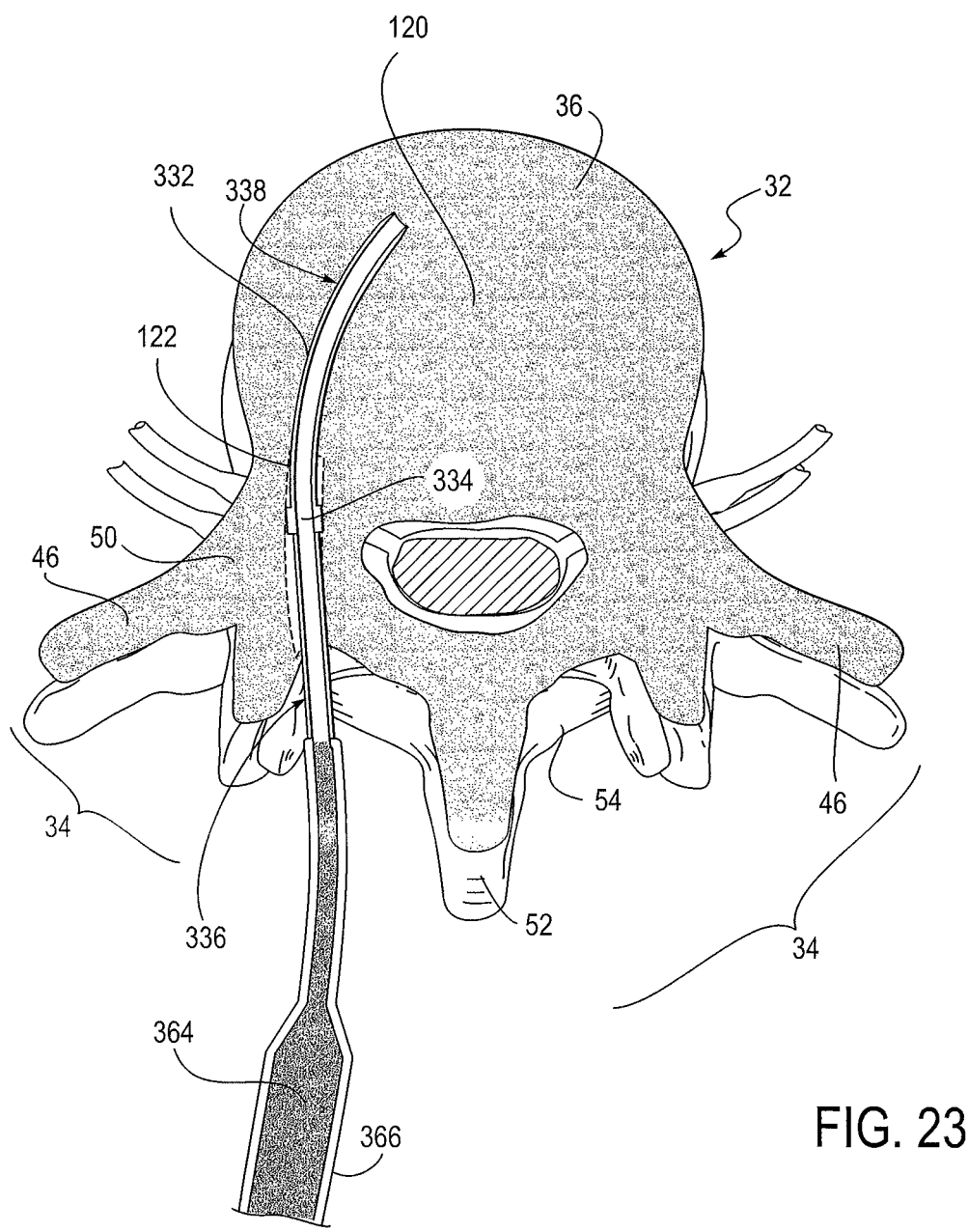
FIG. 23 is an elevational view, showing the attachment of a delivery device to the elongate member of FIG. 22 for use in delivery of a material into the interior of the vertebra.

An introducing device 366 having a solidifying agent 364 or other material therein or capable of receipt thereof, may then be attached to the posterior end 346 of the cannulated posterior spinal fastener or elongate member 332 as shown in FIG. 23. The introducing device, or an opening thereof, is placed in communication with the centralized bore 334 of the cannulated member for transmission of the solidifying agent 364 or material into and through the elongate cannulated member.

As indicated, the cannulated member, and specifically bore 334 allows the application of various medicaments, materials, substances, and/or tools. For instance, other devices or tools, may be inserted directly through bore 334 into the interior of the vertebra. Alternatively, materials, or medicaments may be introduced into the vertebra through the cannulated member, such as by use of a syringe or delivery device attached to the cannulated member. For instance, an adhesive of cement or solidifying material 364 may be introduced into the vertebral body 36. As a non-limiting example, a solidifying material or agent 364 may be introduced into the vertebra 32, and preferably a central portion 120 of the vertebra 32, using a cannulated fastener 330 as shown in FIGS. 23-27 to inhibit unwanted pullout of the posterior spinal fastener. Specifically, the method includes introducing a solidifying agent 364 through the bore 334 in the fastener into the vertebral body 36 to inhibit unwanted pullout of the fastener.

Figure 24:
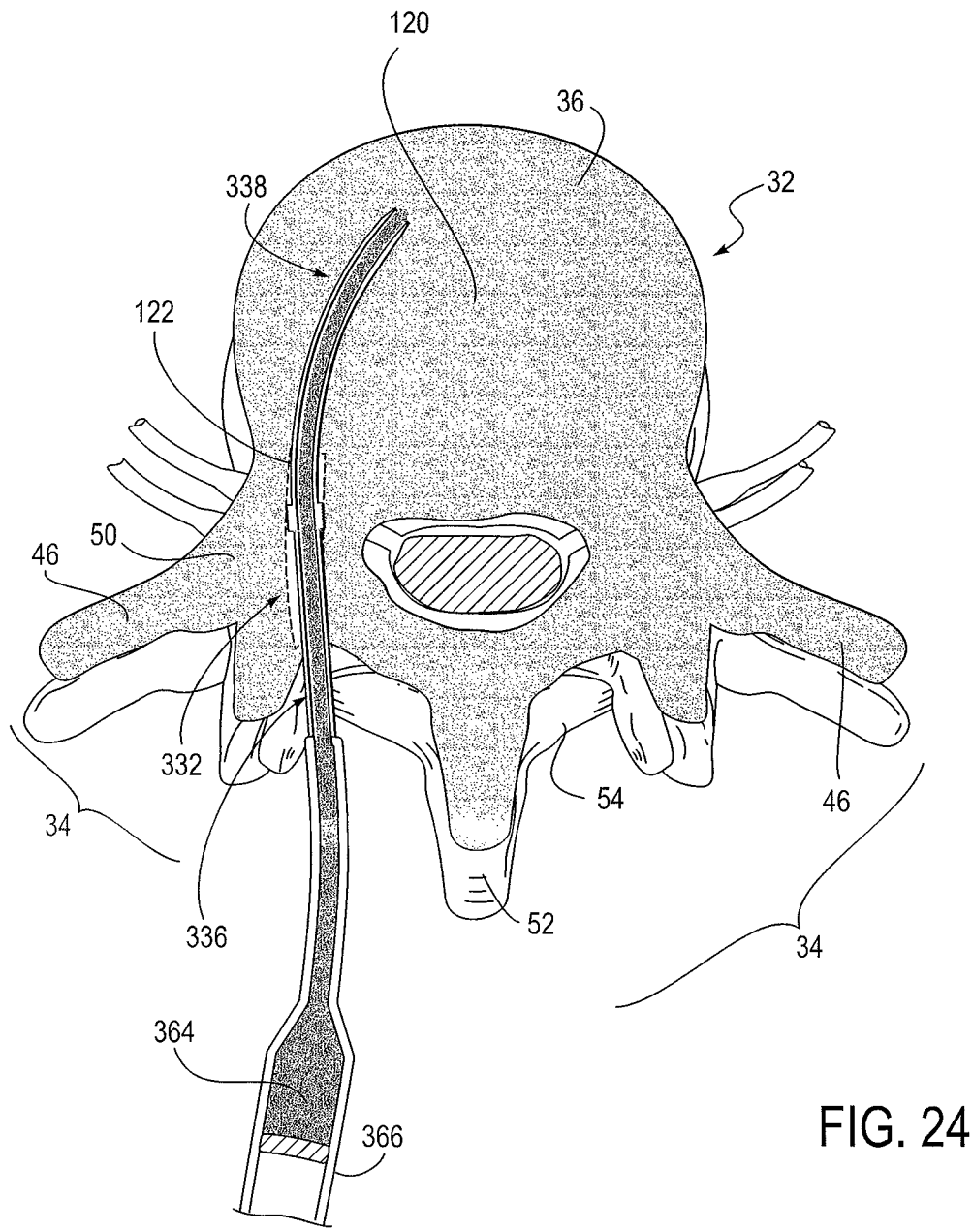
FIG. 24 is an elevational view, showing the attachment of a delivery device to the elongate member of FIG. 22 in which material is delivered through the delivery device and elongate member of FIG. 23, the material provided in a first partially injected position into the interior of the vertebra.
Figure 25:
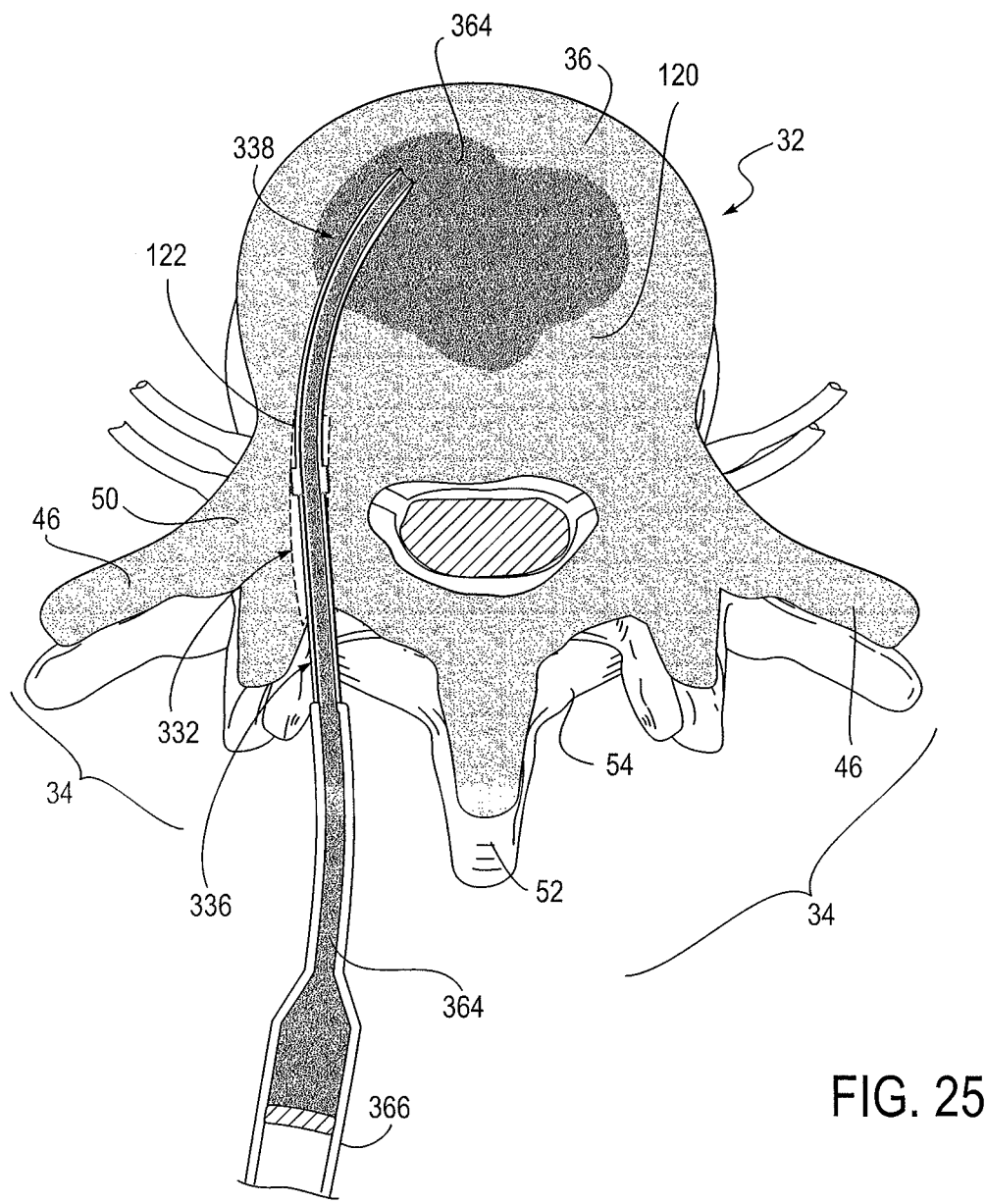
FIG. 25 is an elevational view showing the attachment of a delivery device to the elongate member of FIG. 22 in which material is delivered through the delivery device and elongate member of FIG. 23 to a second position into the interior of the vertebra.

The material 364 is transferred from the syringe 366 through the cannulated member's central bore 334 as shown in FIG. 24 and into the vertebral body. Transfer may be accomplished by suitable means related to the introducing device 366 chosen, such as the use of a syringe having a plunger thereon, which plunger may be used or pressed or vibrated to force the transfer of material. Continued introduction of material 364 or force causes the material to travel from the syringe 366, into the posterior end of the cannulated member and through the opening formed by the bore 334 in the anterior end of the cannulated member 332 into the vertebral body 36 (FIG. 25). Material 364 may also be introduced into the vertebral body through additional or alternative apertures or fenestrations 356 (see FIG. 18) spaced along the shaft of the elongate cannulated member 332 where applicable. Preferably, an amount of cement material suitable for anchoring the elongate member 332 is placed within the vertebral body. The amount of material introduced can range from 0.01 cc to 150 cc and more preferably from 1 cc to 30 cc.

In the vertebral body 36, the solidifying agent 364 hardens and forms an anchor for the anterior portion 338 of the elongate member 332 and therefore the posterior spinal fastener 330 which is in contact with or at least partially surrounded by the introduced solidifying agent 364 in the vertebral body 36. The solidifying agent can also increase the density of the vertebral body and help in filling voids, increase the structural stability, and recreate the anatomy of the vertebral body if collapsed due to fracture, tumor, or other pathologic condition.

Figure 26:
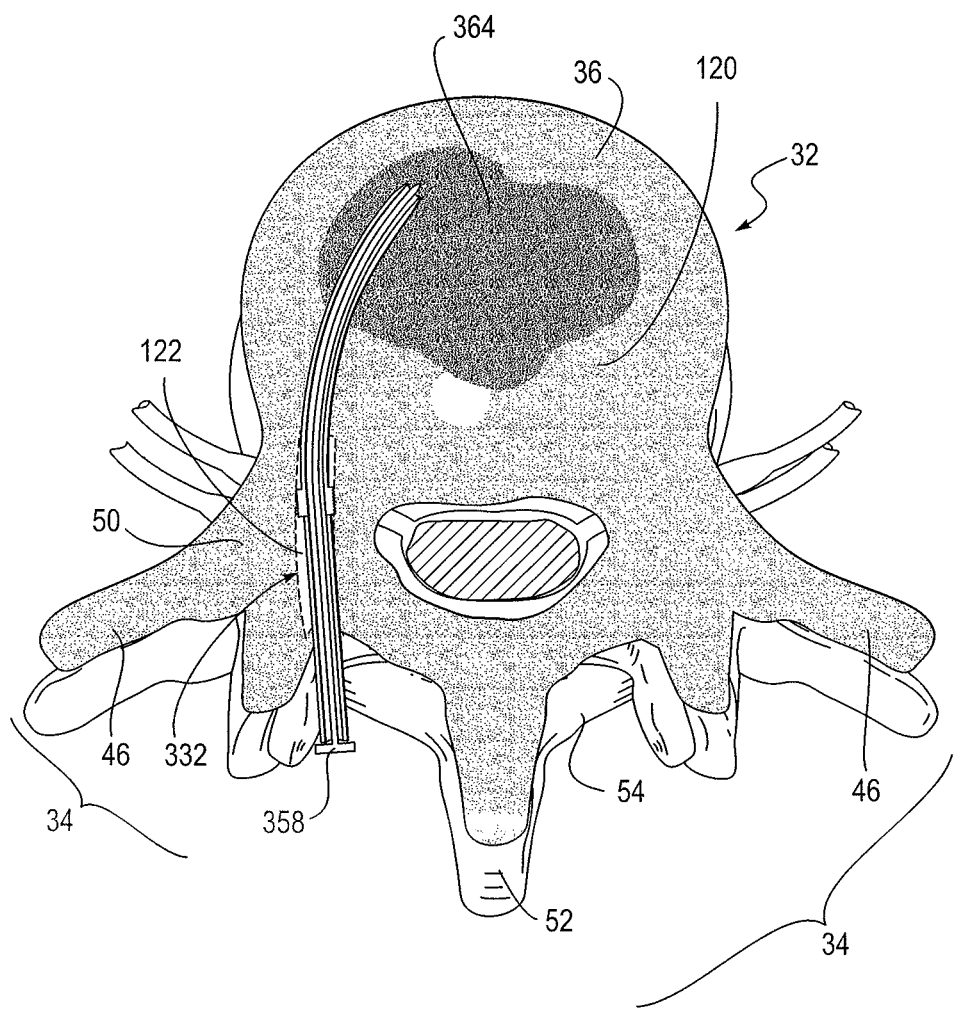
FIG. 26 is an elevational view showing the elongate member of FIG. 22 with the delivery device removed from the elongate member and reinsertion of the stylet, in which material is in the interior of the vertebra.
Figure 27:
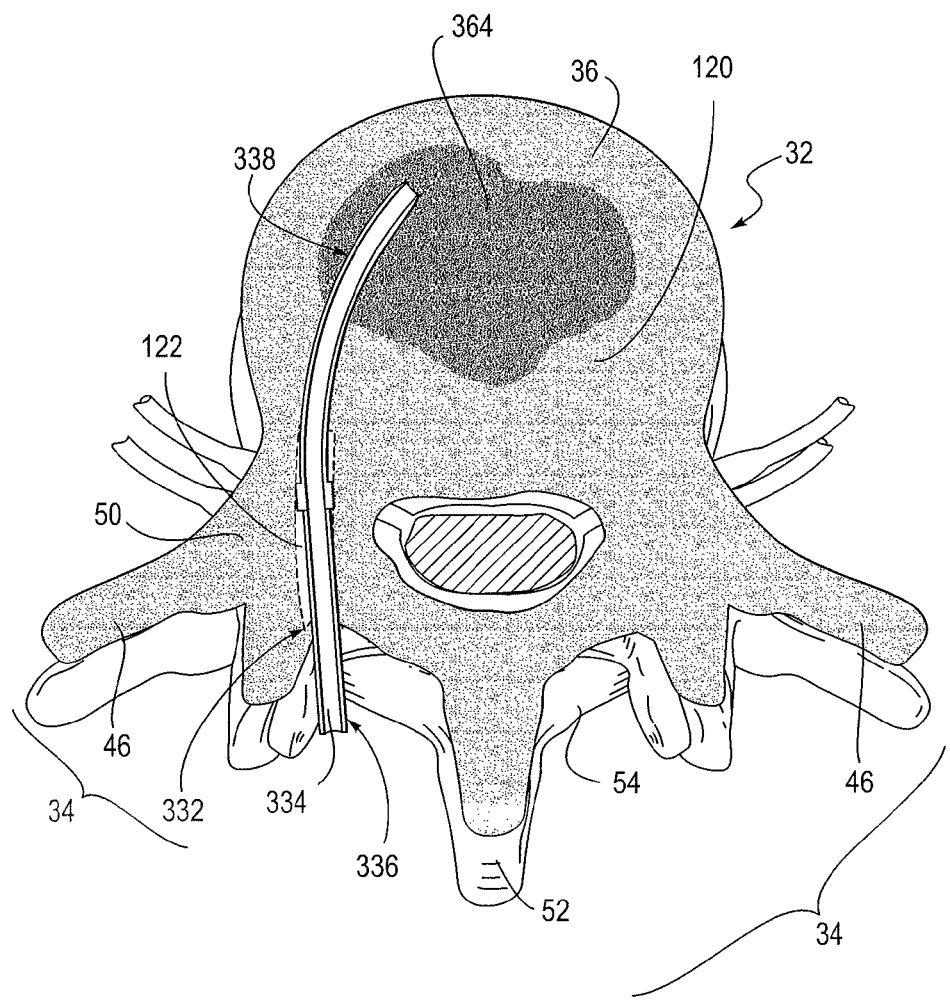
FIG. 27 is an elevational view showing the stylet removed from the elongate member of FIG. 26.

Once introduction of the solidifying agent 364 is completed, the introducing device 366 is detached from the cannulated member 332. The stylet 358 may then be reinserted into the centralized bore 334 of the cannulated member, as shown in FIG. 26, to clean the interior of the bore 334. More specifically, the stylet 358 forces any residual solidifying agent 364 or other material in the bore 334 to exit the bore. The stylet 358 may then, again, be removed, as shown in FIG. 27.

Figure 28:
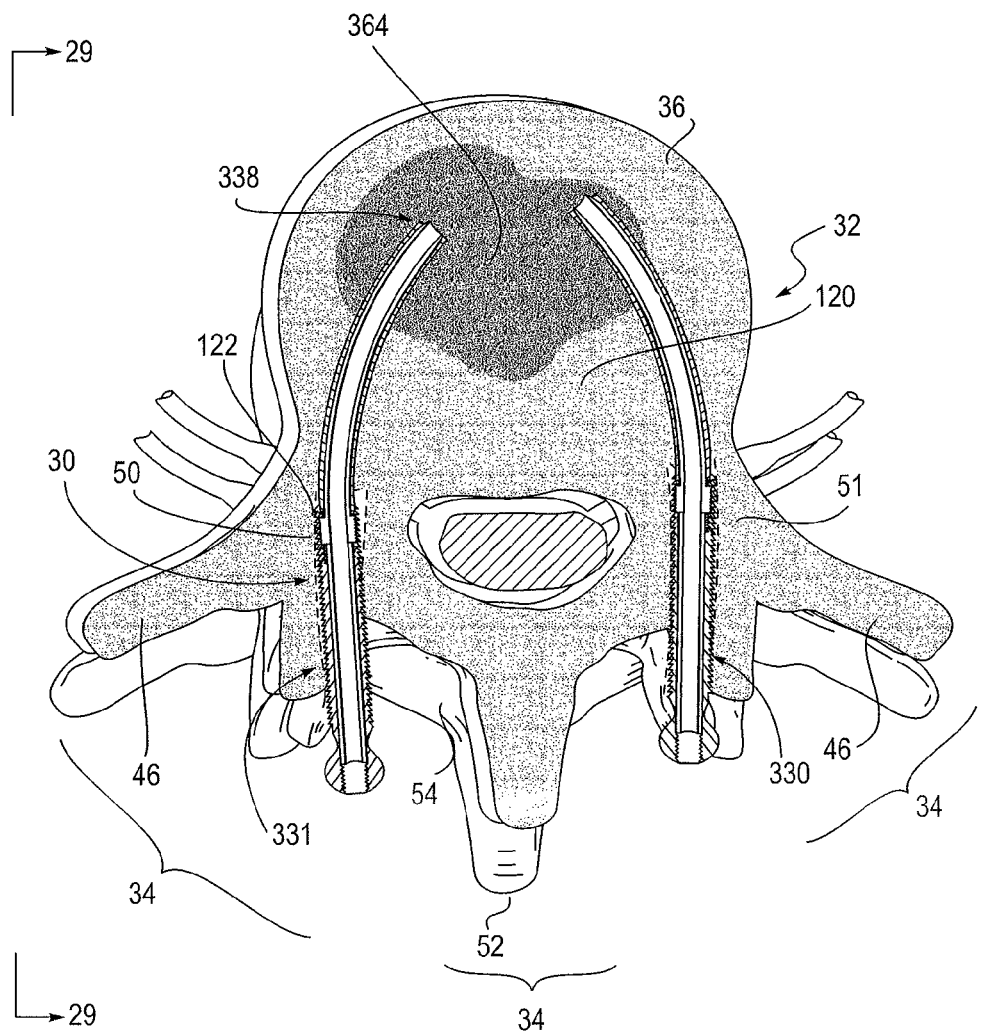
FIG. 28 is an elevational view showing the elongate member of FIG. 18 having a posterior oversleeve thereon, and a second elongate member of FIG. 18 having a posterior oversleeve thereon, each inserted into the vertebra with a material in the interior of the vertebra.
Figure 29:
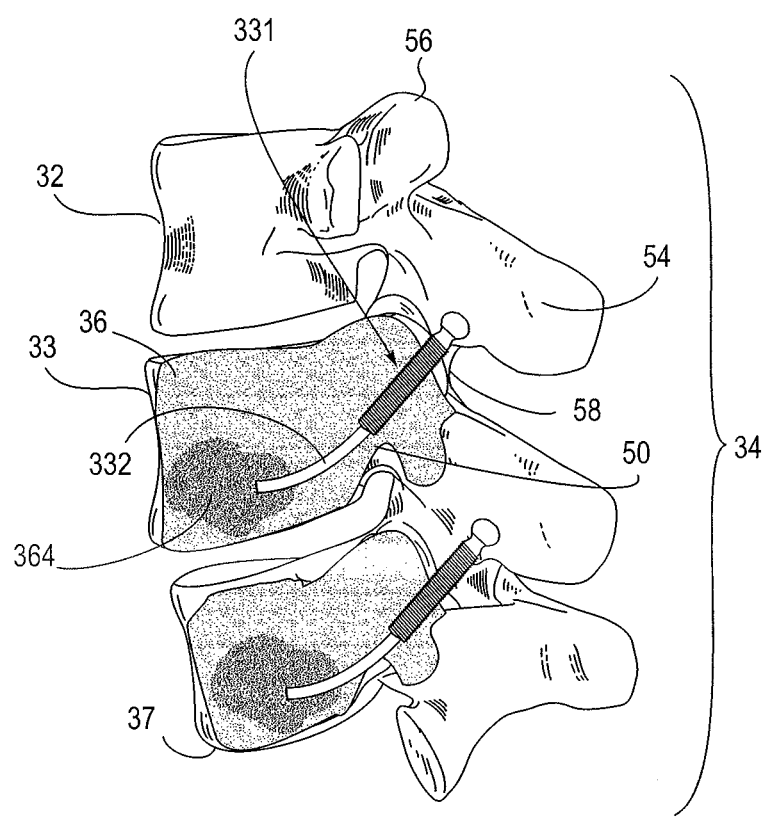
FIG. 29 is an elevational view taken along line 29-29 of FIG. 28, showing inserted elongate members of FIG. 28 in a lamino-pedicle position having threaded oversleeves mounted thereon and additional posterior spinal fasteners in adjacent vertebra.
Figure 30:
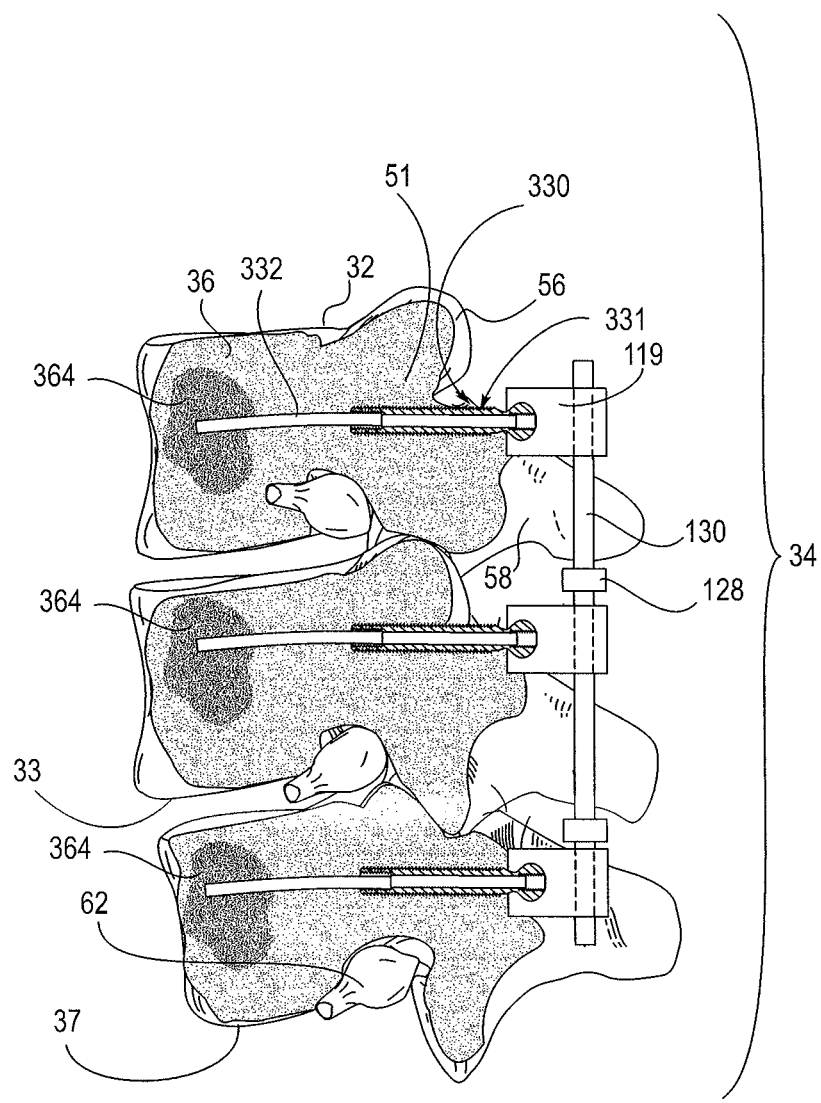
FIG. 30 is an elevational view showing the elongate member of FIG. 18 having a posterior oversleeve thereon and a second elongate member of FIG. 18 having a posterior oversleeve thereon, each inserted into the vertebra in a transpedicle position with a material in the interior of the vertebra.

More than one posterior spinal fastener 330 may be inserted in a vertebra 32 using the foregoing method, as illustrated in FIGS. 28-30. Insertion occurs substantially as described with respect to the previously described embodiments of FIGS. 4-27. In this embodiment solidifying agent 364 may also be introduced through the additional spinal fastener 331 into the central portion 120 of the vertebral body 36 substantially as described with respect to FIGS. 23-27 so that the solidifying agent 364 introduced through the first-named spinal fastener 330 combines with the solidifying agent 364 introduced through the additional spinal fastener 331 and thus couples the first-named spinal fastener to the additional spinal fastener within the vertebral body 36.

As can be seen in FIGS. 28-30, a threaded oversleeve 102 may also be optionally screwed or threaded onto the posterior aspect or portion 336 of the elongate cannulated member 332 and advanced into the arcuate bore in the pedicle 50 substantially as described with respect to the embodiments of FIGS. 4-15. As described with respect to the foregoing embodiments, in its fully inserted position, the threaded oversleeve 102 has its anterior end 106 positioned within the channel 122 formed in the pedicle 50, and its posterior end 104 having the spherical portion 114 extending out of the pedicle 50 and accessible.

The plurality of posterior or curved spinal bone fasteners 330, 331 may also be connected to each other by a variety of mechanisms known in the art and substantially as described herein. The additional fastener may be coupled to the first-named fastener so as to enhance joinder of the fasteners and/or enhance joinder of the first vertebra 32 to the adjacent vertebra 33.

The cannulated posterior spinal fastener 330, like the previously described embodiments, has several advantages over traditional pedicle screws. For example, as with previous embodiments, there is less risk that the posterior fastening device will penetrate the sidewall of the pedicle 50 and contact the nerve because of the smaller external diameter of the fastening device as compared to currently used screws. Likewise, the curved posterior fastening device is not directly dependent upon the density of the bone as related to the pullout strength of the screw, replacing sheer pullout forces of traditional pedicle screws with compression pullout forces. The external threads on the threaded oversleeve 102 also add to the pullout resistance force caused by those threads engaging the inner portion of the pedicle 50. In addition, the cannulated posterior spinal fastener 330 permits the introduction of medicaments and/or devices, as well as other anchoring materials, such as a solidifying agent 364, for further securing the fastener in place in the vertebra 32. Furthermore, each of the fasteners may be arranged into a combined assembly providing a means of an enhancing joinder of adjacent vertebra and requiring more force to pull the claw or fastening devices out.

While specific ranges and dimensions are set forth herein as examples, it will be understood that the assemblies and individual components may be tailored to specific applications and user preferences. To this end the assemblies and individual components may be provided in different sizes to fit different places in the spinal column. Likewise, the implants may also be used to connect the spine to the sacrum and ilium, in which position, the implants generally may be a lot larger and longer. As one example, such an implant can range up to 150 mm in length or more and can be at least ten to 15 millimeters in diameter.

Although various representative embodiments of this invention have been described above with a certain degree of particularity, those skilled in the art could make numerous alterations to the disclosed embodiments without departing from the spirit or scope of the inventive subject matter set forth in the specification and claims. Joinder references (e.g., attached, coupled, connected) are to be construed broadly and may include intermediate members between a connection of elements and relative movement between elements. As such, joinder references do not necessarily infer that two elements are directly connected and in fixed relation to each other. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to preferred embodiments, persons skilled in the art will recognize that changes may be made in form and detail without departing from the spirit and scope of the invention.

What is claimed is:

1. A posterior spinal fastener for securing to a single vertebra of a mammalian body having a vertebral body and posterior elements that include a pedicle and for use with a fastening member comprising an elongate member adapted for insertion into the vertebra, the elongate member having an anterior portion and a posterior portion, the anterior portion being arcuate in shape for placement in the vertebral body, the posterior portion being substantially straight and being sufficiently elongated to extend through the pedicle so as to permit placement of the anterior portion in the vertebral body, at least a portion of the posterior portion being externally threaded for securing the elongate member within the posterior elements when the anterior portion is disposed in the vertebral body and the posterior portion having a head accessible outside of the posterior elements when the anterior portion is disposed in the vertebral body for coupling to the fastening member.

2. The fastener of claim 1 wherein the posterior portion includes a removable threaded oversleeve that is substantially straight.

3. The fastener of claim 1 wherein the elongate member is provided with a bore extending longitudinally therethrough.

4. The fastener of claim 3, wherein the posterior portion has an end provided with a connector adapted to receive a syringe.

5. The fastener of claim 3 wherein the anterior portion is fenestrated.

6. The fastener of claim 1, wherein the elongate member includes an elongate body having an anterior portion and an oversleeve positionable over the anterior portion of the elongate body.

7. The fastener of claim 6, wherein the oversleeve has an arcuate shape.

8. The fastener of claim 6, wherein the posterior portion includes an additional removable oversleeve.

9. The fastener of claim 8, wherein the additional removable oversleeve is removeably engaged with the first-named removable oversleeve.

10. The fastener of claim 1, wherein the elongate member is rigid.

11. The fastener of claim 1, wherein the elongate member includes an elongate body and an oversleeve, the elongate body being elastic.

12. The fastener of claim 11, wherein the elastic elongate body is formed of a shape memory material.

13. A posterior spinal fastener for securing to a single vertebra of a mammalian body having a vertebral body and posterior elements that include a pedicle comprising an elongate element adapted for insertion into the vertebra, the elongate element having a central axis and an anterior portion and a posterior portion, the anterior portion being elastic, a curved oversleeve distinct from the posterior portion disposed over the anterior portion for arcuately guiding the anterior portion into the vertebral body and being implanted into the vertebral body, the anterior portion being rotatable about the central axis within the curved oversleeve for screwing the anterior portion into the vertebral body, the posterior portion having at least a portion disposed in the posterior elements and being sufficiently elongated so as to extend through the pedicle and be accessible outside the posterior elements when the anterior portion is disposed in the vertebral body.

14. The fastener of claim 13 for coupling to a fastening member, the posterior portion having a head accessible outside of the posterior elements when the anterior portion is disposed in the vertebral body for coupling to the fastening member.

15. The fastener of claim 13, wherein the posterior portion is substantially straight.

16. The fastener of claim 13, wherein the posterior portion includes a removable threaded oversleeve.

17. A posterior spinal fastener for securing to a single vertebra of a mammalian body having a vertebral body and posterior elements that include a pedicle comprising an elongate element adapted for insertion into the vertebra, the elongate element having a central axis and an anterior portion and a posterior portion, the anterior portion being elastic, a curved oversleeve distinct from the posterior portion disposed over the anterior portion for arcuately guiding the anterior portion into the vertebral body and being implanted into the vertebral body, the anterior portion being rotatable about the central axis within the curved oversleeve and having a threaded tip for permitting screwing of the anterior portion into the vertebral body, the posterior portion having at least a portion disposed in the posterior elements and being sufficiently elongated so as to extend through the pedicle and be accessible outside the posterior elements when the anterior portion is disposed in the vertebral body.

18. The fastener of claim 17, wherein the posterior portion is substantially straight.

19. The fastener of claim 17, wherein the posterior portion includes a removable threaded oversleeve.

* * * * *